US010156547B2

(12) United States Patent
Biesak et al.

(10) Patent No.: US 10,156,547 B2
(45) Date of Patent: Dec. 18, 2018

(54) METHOD AND APPARATUS FOR PROVIDING REAL TIME AIR MEASUREMENT APPLICATIONS IN WET CONCRETE

(71) Applicant: CiDRA Corporate Services Inc., Wallingford, CT (US)

(72) Inventors: John Biesak, Durham, CT (US); Douglas H. Loose, Southington, CT (US); Michael A. Davis, Glastonbury, CT (US)

(73) Assignee: CiDRA Corporate Services Inc., Wallingford, CT (US)

( * ) Notice: Subject to any disclaimer, the term of this patent is extended or adjusted under 35 U.S.C. 154(b) by 1006 days.

(21) Appl. No.: 14/350,711

(22) PCT Filed: Oct. 18, 2012

(86) PCT No.: PCT/US2012/060822
§ 371 (c)(1),
(2) Date: Apr. 9, 2014

(87) PCT Pub. No.: WO2013/059466
PCT Pub. Date: Apr. 25, 2013

(65) Prior Publication Data
US 2014/0297204 A1 Oct. 2, 2014

Related U.S. Application Data

(60) Provisional application No. 61/548,549, filed on Oct. 18, 2011, provisional application No. 61/548,563, filed on Oct. 18, 2011.

(51) Int. Cl.
*G01N 29/024* (2006.01)
*G01F 17/00* (2006.01)
(Continued)

(52) U.S. Cl.
CPC ............ *G01N 29/024* (2013.01); *G01F 1/74* (2013.01); *G01F 17/00* (2013.01);
(Continued)

(58) Field of Classification Search
CPC .................................................... G01N 29/024
See application file for complete search history.

(56) References Cited

U.S. PATENT DOCUMENTS 4,688,578 A    8/1987   Takano et al.
4,943,930 A    7/1990   Radjy
(Continued)

FOREIGN PATENT DOCUMENTS

DE      3210173       9/1983
EP      00493946      12/1991
(Continued)

OTHER PUBLICATIONS

Stencel J M et al: "Automated foam index test: Quantifying air entraining agent addition and interactions with fly ash-cement admixtures", Cement and Concrete Research, Pergamon Press, Elmsford, NY, US, vol. 39, No. 4, Apr. 1, 2009 J.Cemconres.2009. 01.010 [retreived on Feb. 20, 2009].
(Continued)

*Primary Examiner* — Manuel A Rivera Vargas
(74) *Attorney, Agent, or Firm* — Ware, Fressola, Maguire & Barber LLP

(57) ABSTRACT

Apparatus is provided having an acoustic-based air probe with an acoustic source configured to provide an acoustic signal into a mixture of concrete; and an acoustic receiver configured to be substantially co-planar with the acoustic source, to respond to the acoustic signal, and to provide signaling containing information about the acoustic signal injected into the mixture of concrete.

68 Claims, 12 Drawing Sheets

(51) Int. Cl.
  *G01F 1/74* (2006.01)
  *G01N 29/24* (2006.01)
  *G01N 29/44* (2006.01)
  *G01N 33/38* (2006.01)
  *G01N 29/42* (2006.01)
  *G01N 29/50* (2006.01)

(52) U.S. Cl.
  CPC ......... *G01N 29/2468* (2013.01); *G01N 29/42* (2013.01); *G01N 29/44* (2013.01); *G01N 29/4436* (2013.01); *G01N 29/4472* (2013.01); *G01N 29/50* (2013.01); *G01N 33/383* (2013.01); *G01N 2291/012* (2013.01); *G01N 2291/02433* (2013.01)

(56) References Cited

U.S. PATENT DOCUMENTS

| | | |
|---|---|---|
| 5,313,405 A | 5/1994 | Jiles et al. |
| 5,650,061 A | 7/1997 | Kuhr et al. |
| 5,883,569 A | 3/1999 | Kolefas |
| 5,924,499 A | 7/1999 | Birchak et al. |
| 6,330,383 B1 | 12/2001 | Cai et al. |
| 6,644,119 B1 | 11/2003 | Sinha |
| 6,724,319 B1 | 4/2004 | Knaack et al. |
| 7,076,227 B1 | 7/2006 | Smith |
| 7,134,320 B2 | 11/2006 | Gysling et al. |
| 7,165,464 B2 | 1/2007 | Gysling et al. |
| 7,343,820 B2 | 3/2008 | Gysling et al. |
| 7,363,800 B2 | 4/2008 | Gysling et al. |
| 7,367,240 B2 | 5/2008 | Gysling et al. |
| 7,425,852 B2 | 9/2008 | Rothman |
| 7,426,852 B1 | 9/2008 | Rothman |
| 2002/0032517 A1 | 3/2002 | Buckelew et al. |
| 2003/0016762 A1 | 1/2003 | Martin et al. |
| 2005/0061060 A1 | 3/2005 | Gysling et al. |
| 2006/0243487 A1 | 11/2006 | Turner et al. |
| 2007/0179653 A1 | 8/2007 | Trost et al. |
| 2008/0208483 A1 | 11/2008 | Loose et al. |
| 2009/0078519 A1 | 3/2009 | Carcaterra et al. |
| 2013/0192351 A1* | 8/2013 | Fernald ................. G01F 1/7082 73/61.49 |

FOREIGN PATENT DOCUMENTS

| | | |
|---|---|---|
| GB | 2116806 | 9/1983 |
| JP | 1983169057 | 10/1983 |
| JP | 1992043961 | 6/1992 |
| JP | 1997257769 | 10/1997 |
| JP | 2000241295 | 9/2000 |
| JP | 2001337074 | 12/2001 |
| JP | 2005201676 | 7/2005 |
| JP | 2008302646 | 6/2008 |
| WO | 2011109769 | 9/2011 |
| WO | 2011119335 | 9/2011 |

OTHER PUBLICATIONS

English-language abstract and machine translation of JP2001337074, a publication date Dec. 7, 2001.
English-language abstract and machine translation of JP1997257769, a publication date Oct. 3, 1997.
English-language abstract and machine translation of JP2005201676, a publication date Jul. 28, 2005.
English-language abstract and machine translation of JP1992043961, a publication date Jun. 11, 1992.
English-language abstract and machine translation of JP2008302646 a publication date Jun. 11, 2008.

* cited by examiner

Apparatus 10:

Signal processor 10a configured to receive signaling containing information about
an acoustic signal injected into a mixture of concrete;

determine a measurement of air percentage
in the mixture of concrete based at least partly on
a dual frequency technique that depends on
a relationship between the acoustic signal injected and
the signaling received, including either by mixing
a reference signal injected with detected signaling
using a phase sensitive lock-in approach, or by correlating
the acoustic signal injected and the signaling received; and/or .

provide corresponding signaling containing information
about the measurement of air percentage in the mixture
of concrete, e.g., that may be used to control the amount of air
in the mixture of concrete by causing the addition or substraction
of some other material or substance to modify air percentage
in the mixture of concrete Other signal processing modules 10b for implementing the signal
processing functionality according to the present invention,
including memory for storing a computer program code,
input/output modules, and data and control busing archetecture
for coupling all the signal processing component together

Figure 4

METHOD AND APPARATUS FOR PROVIDING REAL TIME AIR MEASUREMENT APPLICATIONS IN WET CONCRETE

CROSS-REFERENCE TO RELATED APPLICATIONS

This application claims benefit to provisional patent application Ser. No. 61/548,549, filed 18 Oct. 2011; and Ser. No. 61/548,563, filed 18 Oct. 2011, which are both incorporated by reference in their entirety.

This application also relates to U.S. patent application Ser. No. 13/583,062, filed 12 Sep. 2012, which is a national stage application corresponding to PCT/US1127731, which are both incorporated in their entirety by reference, and assigned to the assignee of the present application.

BACKGROUND OF THE INVENTION

1. Field of Invention

The present invention relates to a technique for real time air measurement in wet concrete; more particularly related to a technique for real time air measurement in wet concrete in order to control the amount of air in a mixture of concrete.

2. Description of Related Art

In the prior art, the use of a method for the determination of the flow rate of the medium through a measurement of the velocity of convecting vortical pressure instabilities, and the composition of a two-phase flow through the determination of the speed of sound of the medium, are known. As the composition of the flow varies between the two extremes of 100% of one fluid to 100% of the other, the speed of sound varies in a deterministic way between the values of sound speed in the two respective materials. In the known techniques, the determination of the speed of sound was made using 'passive' listening of the sound propagating in the flow stream.

In the prior art, a number of techniques have been developed that rely on measuring the speed of sound through a material flowing through a pipe. These techniques include using a known SONAR-based GVF meter, density meter and potential mass fraction meter. In these techniques, a passive array-based sensor system is used to detect the presence and speed of acoustics traveling through the materials contained within a pipe. These materials can range from single phase homogeneous fluids to two or three phase mixtures of gases, liquids and solids. Since the measurements system is passive it relies on acoustics produced externally for the measurement. These acoustics can often times come from other equipment in or attached to the pipe such as pumps or valves.

Moreover, in these known techniques many times chemical additives may be added, including to a known flotation process in mineral processing to aid in the separation of the ore. The chemicals, known as frothers, control the efficiency of the flotation process by enhancing the properties of the air bubbles. An important parameter in flotation optimization is the gas volume fraction within a flotation cell. U.S. Pat. No. 7,426,852 B1, which is hereby incorporated by reference in its entirety, discloses approaches to make this measurement, and discloses a technique whereby the speed of sound in the aerated fluid is locally measured using a waveguide (pipe) in conjunction with a SONAR-based array. From the speed of sound measurement, the gas volume fraction can be calculated.

By way of example, see other techniques related to the use of such SONAR-based technology disclosed, e.g., in whole or in part in U.S. Pat. Nos. 7,165,464; 7,134,320; 7,363,800; 7,367,240; and 7,343,820, all of which are incorporated by reference in their entirety.

Moreover, air is a very important component of many materials, such as viscous liquids, slurries or solids, and mixtures of concrete. In particular, air is a critical ingredient when making concrete because it greatly improves the cured product damage resistance to freeze/thaw cycles. Chemical admixtures are typically added during mixing to create, entrain and stabilize billions of small air bubbles within the concrete. However, the entrained air in concrete has the disadvantage of reducing strength so there is always a trade-off to determine the right amount of air for a particular application. In order to optimize certain properties of concrete, it is important to control the entrained air present in the wet (pre-cured) concrete. Current methods for measuring the entrained air can sometimes be slow and cumbersome and additionally can be prone to errors. Moreover, the durability of concrete may be enhanced by entraining air in the fresh mix. This is typically accomplished through the addition of chemical admixes. The amount of admix is usually determined through empirical data by which a "recipe" is determined. Too little entrained air reduces the durability of the concrete and too much entrained air decreases the strength. Typically the nominal range of entrained air is about 5-8% by volume, and can be between 4% and 6% entrained air by volume in many applications. After being mixed in the mixer box, the concrete is then released to the truck. The level of entrained air is then measured upon delivery of the mix to the site. The draw back of the current method is that the mix is committed to the truck without verification of that the air level in the mix is within specification.

The aforementioned U.S. patent application Ser. No. 13/583,062 (WFVA/CiDRA file nos. 712-2.338-1/CCS-0033, 35,40, and 45-49) discloses techniques for real time air measurement in wet concrete in concrete a rotary drum mixer, including implementing sensing technology in a hatch cover, as well as a stationary concrete mixer using an integrated sound source and two receivers, using SONAR-based technology developed and patented by the assignee of the instant patent application as well as that application.

SUMMARY OF THE INVENTION

CCS-0075

The present application provides new means, techniques or ways of real time measurement of entrained air in wet concrete, consistent with and further building on that set forth in the aforementioned U.S. patent application Ser. No. 13/583,062, filed 12 Sep. 2012 (WFVA/CiDRA file nos. 712-2.338-1/CCS-0033, 35,40, and 45-49).

By way of example, the present invention provides new measurement devices that may include, or take the form of, acoustic-based air probes, e.g., that may be permanently installed in a precut hole on the side or bottom of a stationary mixer, or alternatively that may be handheld for taking the real time measurement. The same or a substantially similar installation technique of installing in the precut hole of the stationary mixer may be used or applied for applications related to a rotating drum style mixer, or other type or kind of mixer, consistent with that disclosed herein. By way of example, these measurement devices according to the present invention may be used for real time air measurement on the stationary mixer (such as a twin shaft, counter current, planetary, pan etc.) during the mixing process. With real time air measurement, an operator will be able to improve the quality control of all concrete produced. Entrained air level in concrete may be controlled to a tighter tolerance. With tight air control, the mix design can be optimized by reducing cement and replacing it with sand, fly ash or another filler, while still achieving the desired strength requirement.

This will reduce cost, improve workability and reduce "bleeding"incidents. There are many types of concrete that are made in stationary mixers, including precast, prestress, architectural, paving, block, ready mix-central mixers primarily in but limited to Europe, etc. All these types of concrete will likely benefit from real time air control, according to the present invention.

With real time air information the operator will now have the ability to adjust the air levels (manually or automatically (via a process control)) through chemical addition prior to dumping the concrete from the mixer. An automatic closed loop system may be used that includes these types of measurement devices with real time air information output to the control room or to the dosing pump, chemical dosing pumps, air related chemicals and the engineering expertise to tie it all together.

The Acoustic-based Air Probe

According to some embodiments, the present invention may include, or take the form of, apparatus featuring an acoustic-based air probe having an acoustic source configured to provide an acoustic signal into a mixture of concrete; and an acoustic receiver configured to be substantially co-planar with the acoustic source, to respond to the acoustic signal, and to provide signaling containing information about the acoustic signal injected into the mixture of concrete.

The present invention may also include, or take the form of, some combination of the following features:

The acoustic-based air probe may include a planar probing surface having a first aperture formed therein configured to receive part of the acoustic source, e.g., a rigid hardened steel piston. The planar probing surface may include at least one second aperture formed therein configured to receive part of the acoustic receiver, e.g., a protective polyurethane rubber fill. The planar probing surface may be configured as a hardened steel face plate.

The acoustic-based air probe may include the protective polyurethane rubber member arranged as the part in the at least one second aperture.

The acoustic receiver may include a dynamic pressure transducer.

The acoustic receiver may be configured to receive acoustic signals having a frequency in a range of about 100-500 Hz, including 330 Hz.

The acoustic source may include, or be configured as, a floating mass.

The acoustic source may include a piston module assembly having the rigid hardened steel piston configured with a channel to receive a piston shaft. The apparatus may include a vibration isolated actuator block assembly having a stationary voice coil actuator field assembly in combination with a voice coil actuator field assembly having an accelerometer transducer, the vibration isolated actuator block assembly being configured to drive the piston shaft.

The acoustic-based air probe may include a fluid/media temperature sensor.

The acoustic-based air probe may include a voice coil temperature sensor.

The acoustic-based air probe may include two acoustic receivers, including two dynamic pressure transducers.

The apparatus may include dosing apparatus configured to respond to the signaling, and provide a control signal to control the dosing of a chemical to be added or subtracted from the mixture.

The present invention can also provide new techniques for real time air measurement applications and techniques for wet concrete, including techniques using, or based at least partly on determining gas volume fraction (GVF) for a mixture of concrete that is ready mixed in a stationary mixer, a rotating drum mixer, a pump boom or truck chute, application forms made in a precast facility, a handheld unit.

For example, the apparatus may include a stationary mixer having a wall with the acoustic-based air probe arranged therein, including where the stationary mixer is configured with a central chemical dosing location to allow for more even distribution of chemicals into the mixing.

The apparatus may include a concrete pump boom having a wall with the acoustic-based air probe arranged therein.

The apparatus may include a precast form having a wall with the acoustic-based air probe arranged therein.

The apparatus may include a ready mix truck rotating drum mixer having a wall with the acoustic-based air probe arranged therein.

The apparatus may include a ready mix truck chute having a wall with the acoustic-based air probe arranged therein.

The acoustic-based air probe may be configured to work in conjunction with a signal processor that is configured to perform one or more of the signal processing functions disclosed herein.

The real time air measurement applications and/or signal processing may include, or take the form of, the following:

For example, the apparatus may include the signal processor that may be configured to receive the signaling containing information about the acoustic signal injected into the mixture of concrete; and determine a gas volume fraction of the mixture of concrete based at least partly on a speed of sound measurement of the acoustic signal that travels through the mixture, using a SONAR-based technique, consistent with that set forth in the aforementioned U.S. patent application Ser. No. 13/583,062, filed 12 Sep. 2012 (WFVA/CiDRA file nos. 712-2.338-1/CCS-0033, 35,40, and 45-49).

Alternatively, the signal processor may be configured to receive the signaling containing information about the acoustic signal injected into the mixture of concrete; and determine the measurement of air percentage in the mixture of concrete based at least partly on the dual frequency technique that depends on the relationship between the acoustic signal injected and the signaling received.

The dual frequency technique may include, or take the form of, the signal processor being configured to determine the measurement of air percentage in the mixture of concrete based at least partly on mixing a reference signal with a detected signaling using a phase sensitive lock-in approach.

Alternatively, the dual frequency technique may include, or take the form of, the signal processor being configured to determine the measurement of air percentage in the mixture of concrete based at least partly on correlating the acoustic signal injected and the signaling received.

According to some embodiments of the present invention, the apparatus may form part of a handheld device, including where the aforementioned acoustic-based air probe is configured on one end of the handheld device and a handle is configured on the other end of the handheld device.

The Handheld Acoustic-based Air Probe

According to some embodiments, the apparatus may also include, or take the form of, a handheld acoustic-based air probe featuring an acoustic source configured to provide an acoustic signal injected into a mixture of concrete; and an acoustic receiver configured to respond to the acoustic signal, and provide signaling containing information about the acoustic signal injected into the mixture of concrete.

The handheld acoustic-based air probe may include one or more of the following features:

The handheld acoustic-based air probe may include at least one spacer strut configured to connect the acoustic source and the acoustic receiver so as to form a space for receiving a portion of the mixture of the concrete when the handheld acoustic-based air probe is dipped into the mixture of concrete and the acoustic signal is transmitted through the mixture. The at least one spacer strut may include, or take the form of, three spacer struts that are triangularly arranged and equally-spaced to connect the acoustic source and acoustic receiver so as to form the space in-between. The at least one spacer strut may include a wiring channel for providing a wire from the acoustic receiver.

The handheld acoustic-based air probe may include a sealed end cap assembly configured to contain the acoustic receiver in a sealing manner.

The handheld acoustic-based air probe may include a sealed assembly configured to contain the acoustic source in a sealing manner. The sealed assembly may include a vibration isolated actuator block configured to actuate the piston source. The vibration isolated actuator block may include a voice coil actuator moving coil assembly with an accelerometer transducer and a stationary voice coil actuator field assembly. The sealed assembly may include hemisphere vibration mounts configured between an alignment cap and the vibration isolated actuator block and also configured between the vibration isolated actuator block and the acoustic source. The sealed assembly may include a spring seal, including a cast urethane spring seal, configured between the acoustic source and an acoustic source retaining member, and a photo-etched flexure configured between the acoustic source and the acoustic source retaining member. The sealed assembly may include a temperature sensor configured to respond to the temperature of the mixture.

The handheld acoustic-based air probe may include a second acoustic receiver configured to respond to the acoustic signal, and provide further signaling containing information about the acoustic signal injected into the mixture of concrete. The second acoustic receiver may be configured on the sealed assembly so as to receive the acoustic signal that is reflected from the mixture of concrete.

The acoustic source and the acoustic receiver may be configured on one end of the handheld acoustic-based air probe. The handheld acoustic-based air probe may include another end configured with some combination of device handles, a normal pressure sensor connector, an accelerometer connector and a temperature and drive connector.

According to some embodiments, the apparatus may also include an acoustic probe apparatus having two acoustic sources configured to provide two reference signals, consistent with that set forth herein.

CCS-0067 and 0104

The Signal Processor of Dual Frequency Techniques

According to some embodiments of the present invention, the apparatus may include, or take the form of, a signal processor configured to receive signaling containing information about an acoustic signal injected into a mixture of concrete; and determine a measurement of air percentage in the mixture of concrete based at least partly on a dual frequency technique that depends on a relationship between the acoustic signal injected and the signaling received.

CCS-0067

Phase Sensitive Dual Frequency Lock-in Measurement for Concrete Air Content with Quality Factor According to some embodiments of the present invention, the dual frequency technique may include the acoustic signal injected being a reference signal; the signaling received being detected signaling; and the signal processor may be configured to determine the measurement of air percentage in the mixture of concrete based at least partly on mixing the reference signal with the detected signaling using a phase sensitive lock-in approach.

According to some embodiment of the present invention, the signal processor may be configured to determine a resulting signal based at least partly on the mixing of the reference signal with the detected signaling; filter the resulting signal, including with a low pass filter, to get a DC component; and determine a value that is proportional to amplitude and phase components of the detected signaling at the frequency of the reference signal. The signal processor may also be configured to determine a corresponding value that is proportional to corresponding amplitude and phase components of the detected signaling with the frequency of reference signal shifted by 90 deg. The signal processor may also be configured to determine a signal phase difference based at partly on the following: using $\Theta ref$ as a reference phase, $\Theta det$ as a detected phase, $Adet$ as a detected signal amplitude at a frequency of interest; and determining a signal amplitude and the signal phase difference using the following set of equations:

$$\Theta = \Theta det - \Theta ref,$$

$$X \sim Adet \cos(\Theta),$$

$$Y \sim Adet \cos(\Theta + 90 deg) = Adet \sin(\Theta),$$

$$\text{Signal amplitude} = Adet = (X^2 * Y^2)^{1/2}, \text{ and}$$

$$\text{Signal phase difference} = \Theta = \tan^{-1}(Y/X).$$

The signal processor may be configured to determine a time of propagation of the reference signal in the mixture of concrete and then a speed of sound measurement, based at least partly on the signal phase difference determined along with the frequency.

According to some embodiment of the present invention, the signaling may contain information about two reference signals that are injected into the mixture of concrete at different frequencies in order correct or compensate for ambiguity that may otherwise exist once the detected signaling has gone though a propagation time equal to 2*pi of a single injected acoustic signal, including any multiple thereof; and the signal processor is configured to determine a relative phase between the two reference signals in order correct or compensate for the ambiguity.

According to some embodiments of the present invention, the signal processor may be configured to determine a quality metric based at least partly on the signal amplitude and signal phase difference determined. For example, the signal processor may be configured to take the signal amplitude of a signal of interest at Asig; take a sample of four other comparison signals spaced adjacent thereto of A0, A1, A2 and A3; average four other comparison signals to obtain an adjacent noise Anoise=(A0+A1+A2+A3)/4; and take a difference over a sum normalization to determine a quality signal, Q, that varies between −1 to 1 based at least partly on using the following equation:

$$Q=(A\text{sig}-A\text{noise})/(A\text{sig}+A\text{noise}),$$

with a ratio of "1" representing a good quality, a ratio of "0" indicating same signal strength at frequency of interest as other frequencies, and a ratio of "−1" as a very weak signal of interest.

CCS-0104

According to some embodiments of the present invention, the dual frequency technique may include the signal processor being configured to determine the measurement of air percentage in the mixture of concrete based at least partly on correlating the acoustic signal injected and the signaling received.

According to some embodiments of the present invention, the signal processor may be configured to determine a phase delay due to a transit of the acoustic signal injected in the mixture of concrete based on the correlating of the acoustic signal injected and the signaling received. The signal processor may be configured to determine the speed of sound based on the phase delay. The signaling containing information about the acoustic signal injected into the mixture of concrete may be based at least partly on using a simple sweep of an excitation frequency to an acoustic actuator, which increases the sensitivity of a correlation process. The simple sweep may be based on the equation:

$$Y(i)=A \sin (ai^2/2+bi).$$

According to some embodiments of the present invention, the signaling containing information about the acoustic signal injected into the mixture of concrete may be based at least partly on one or more techniques of encoded pulsing that are used to alternatively enhance the signal-to-noise of a detected acoustic signal. The encoded pulsing may be based at least partly on a pseudo-random sequence (PRBS), where the PRBS is defined as a sequence of N bits where an autocorrelation of the sequence gives a number proportional to the number of "on" bits times the sequence length when there is no misalignment and a low number proportional to only the number of on bits when misaligned. The PRBS in the case of free-space acoustic measurements may be based at least partly on PRBS excitation that can be created by turning on and off an excitation acoustic wave according to the PRBS sequence, or by frequency modulating the acoustic signal by the PRBS sequence. The signaling containing information about the acoustic signal injected into the mixture of concrete may be based at least partly on frequency encoding, including m-sequence codes or frequency shift keying approaches.

Methods

According to some embodiments of the present invention, the present invention may take the form of a method that may include, or take the form of, steps for receiving in a signal processor signaling containing information about an acoustic signal injected into a mixture of concrete; and determining in the signal processor a measurement of air percentage in the mixture of concrete based at least partly on a dual frequency technique that depends on a relationship between the acoustic signal injected and the signaling received. According to some embodiments of the present invention, the method may include determining in the signal processor the measurement of air percentage in the mixture of concrete based at least partly on mixing a reference signal with a detected signaling using a phase sensitive lock-in approach. According to some embodiments of the present invention, the method may include determining in the signal processor the measurement of air percentage in the mixture of concrete based at least partly on correlating the acoustic signal injected and the signaling received. These methods may also include one or more of the features set forth herein.

According to some embodiments of the present invention, the method may include, or take the form of, steps for vibrating with one part of a handheld vibration assembly a wet concrete medium; and responding with another part of the handheld vibration assembly to the wet concrete medium being vibrated in order to provide signaling containing information about the wet concrete medium being vibrated to be used to determine entrained air in the wet concrete medium.

This method may also include some combination of the following features:

The signaling may be provided as output signaling from on the handheld vibration assembly to be received and used by a signal processor to determine entrained air in the wet concrete medium.

The step of vibrating may include actuating a vibration isolated actuator block assembly that forms part of the handheld vibration assembly.

The method may also include responding to the concrete medium being vibrated with at least one pressure transducer that forms part of the handheld vibration assembly, or providing from the at least one pressure transducer the signaling, or responding to the vibrating concrete medium with two pressure transducers that forms part of the handheld vibration assembly, and/or providing the signaling from the two pressure transducers.

The method may also include determining a measurement of the entrained air in wet concrete, including using SONAR-based technique to determine the measurement.

The method may include adding chemicals to control the entrained air in wet concrete based at least partly on the signaling.

The signaling may be wireless signaling.

The signaling may be displayed on the handheld vibration assembly.

The signal processor may be configured with at least one processor and at least one memory including computer program code, the at least one memory and computer program code configured, with the at least one processor, to cause the apparatus at least to determine the entrained air in the wet concrete medium.

The method may include responding to a user command containing information about vibrating with the handheld vibration assembly the wet concrete medium.

The user command may include input signaling received by the handheld vibration assembly.

The user command may be provided by pressing a button on the handheld vibration assembly.

The method may include vibrating a floating mass that forms part of a vibration isolated actuator assembly at a frequency in a range of about 100-500 Hz.

The present invention makes important contributions to this current state of the art for real time air measurement in wet concrete, as well as techniques to control the amount of air in a mixture of concrete.

BRIEF DESCRIPTION OF THE DRAWING

The drawing includes FIGS. 1-6c, which are not necessarily drawn to scale, as follows:

FIG. 1b is an axial view of one end the acoustic probe shown in FIG. 1a.

FIG. 1c is an axial view of another end the acoustic probe shown in FIG. 1a.

FIG. 4 is a block diagram of apparatus having a signal processor, according to some embodiment of the present invention.

DETAILED DESCRIPTION OF BEST MODE OF THE INVENTION

Figure 1A:
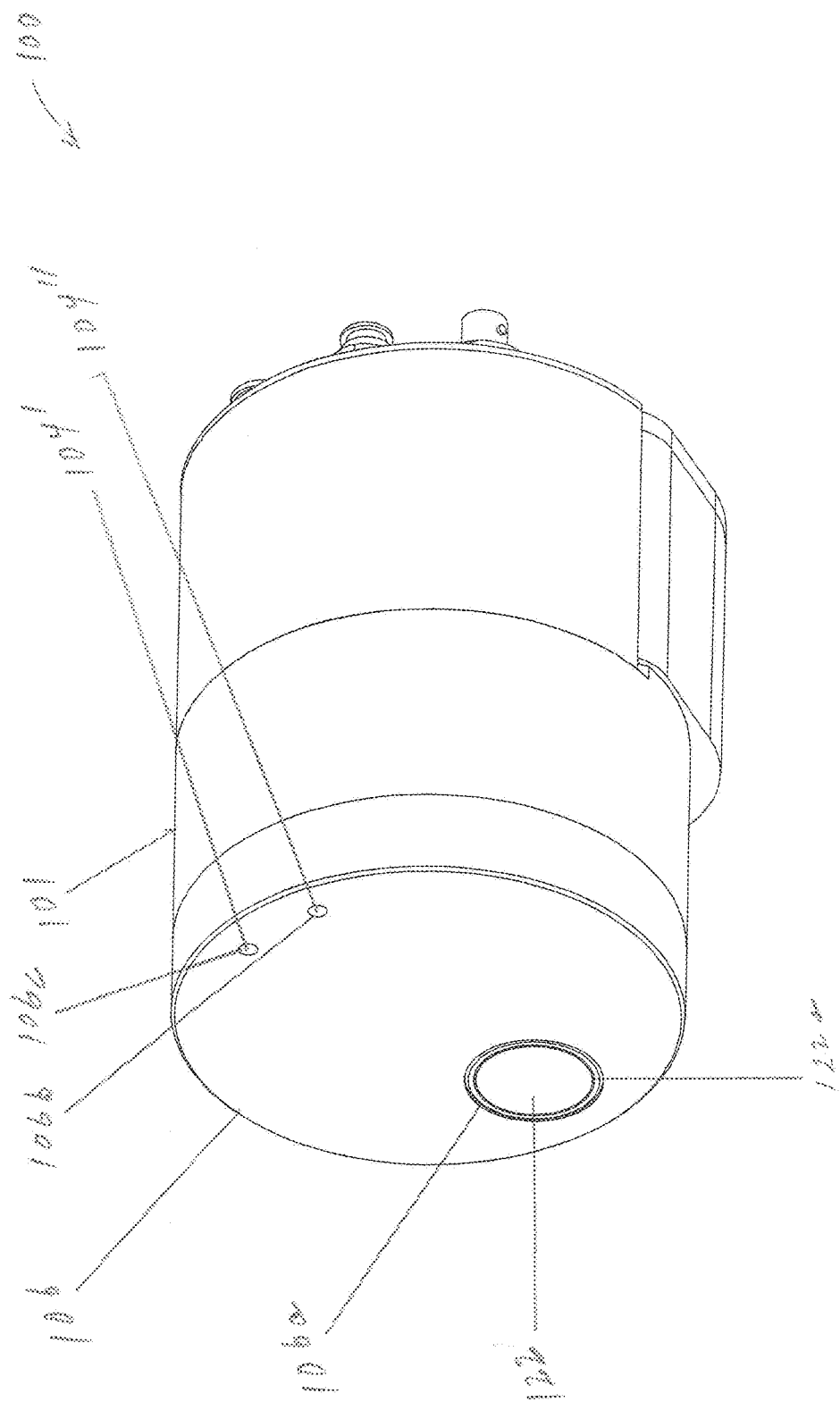
FIG. 1a is a perspective view of an acoustic probe that may implemented some embodiments of the present invention.
Figure 1B:
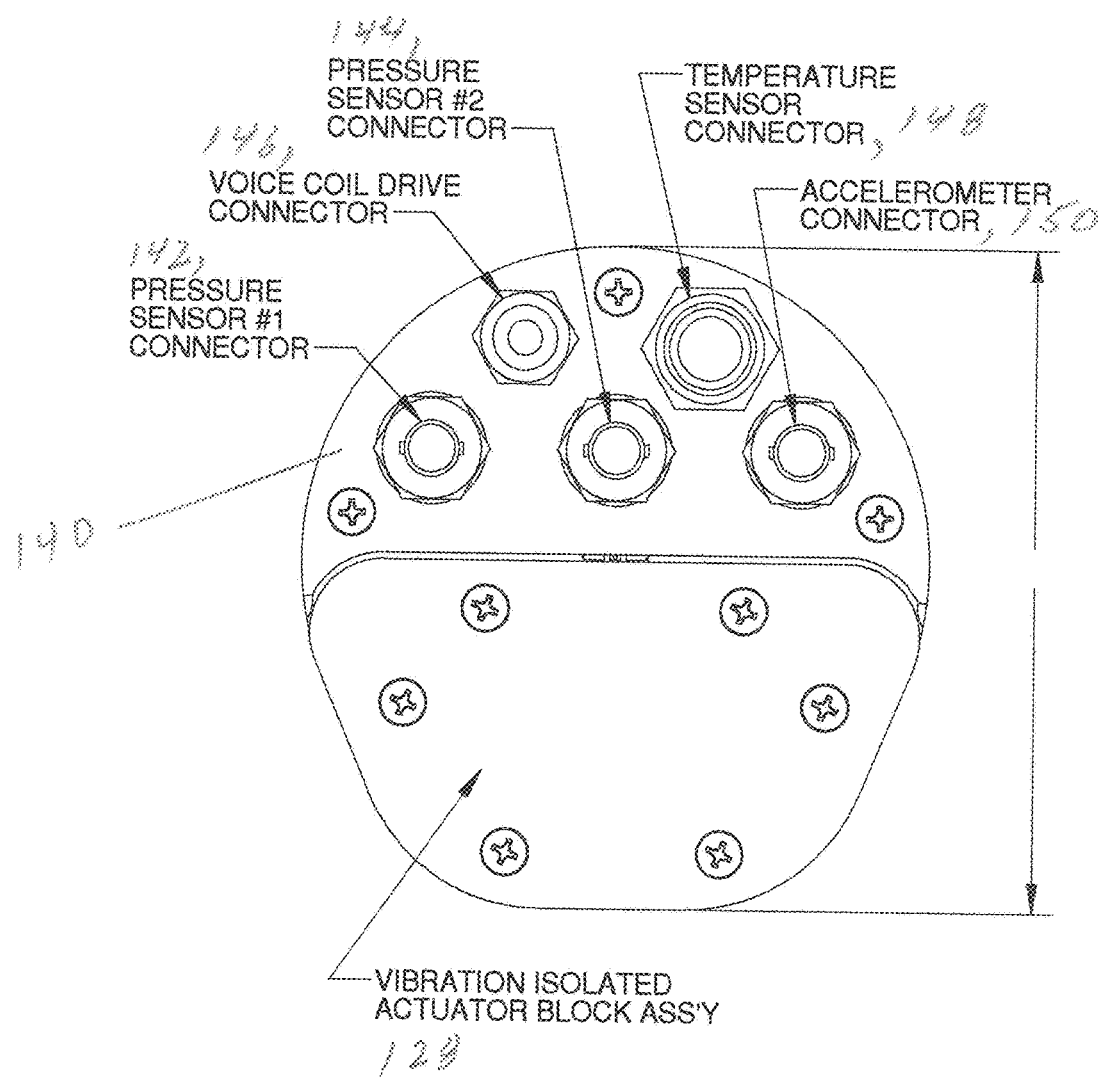
Figure 1C:
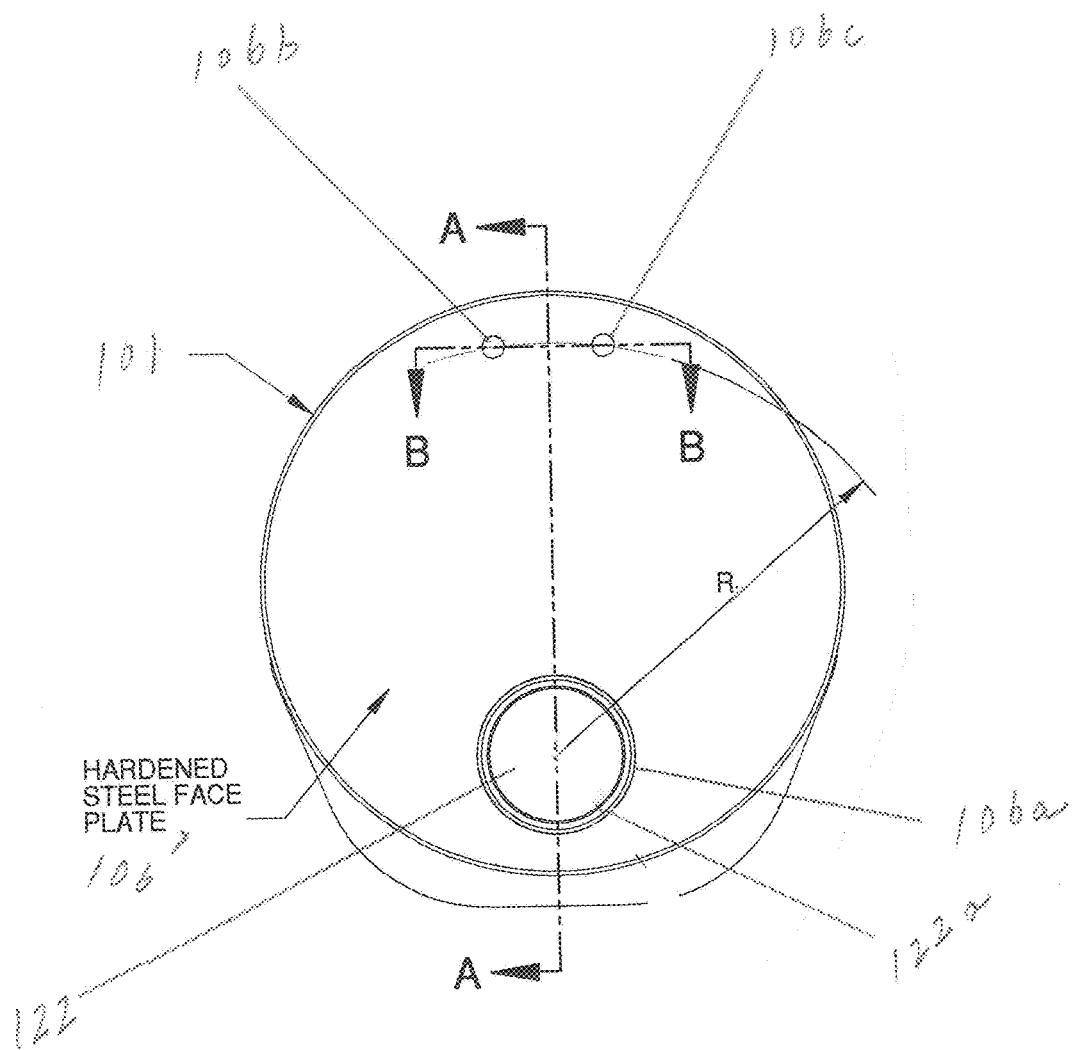
Figure 1D:
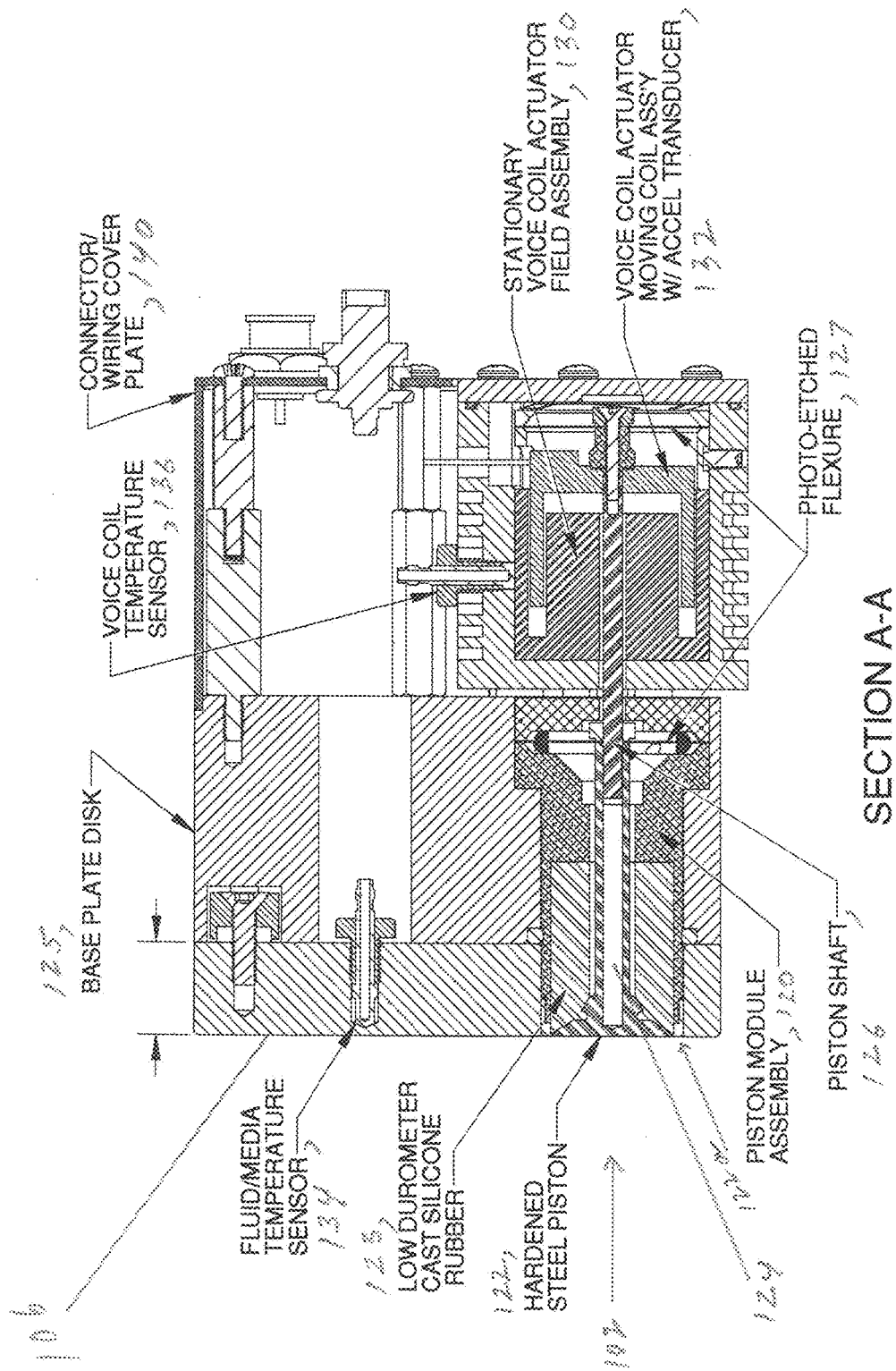
FIG. 1d is a sectional view of the end the acoustic probe shown in FIG. 1c along section lines A-A.
Figure 1E:
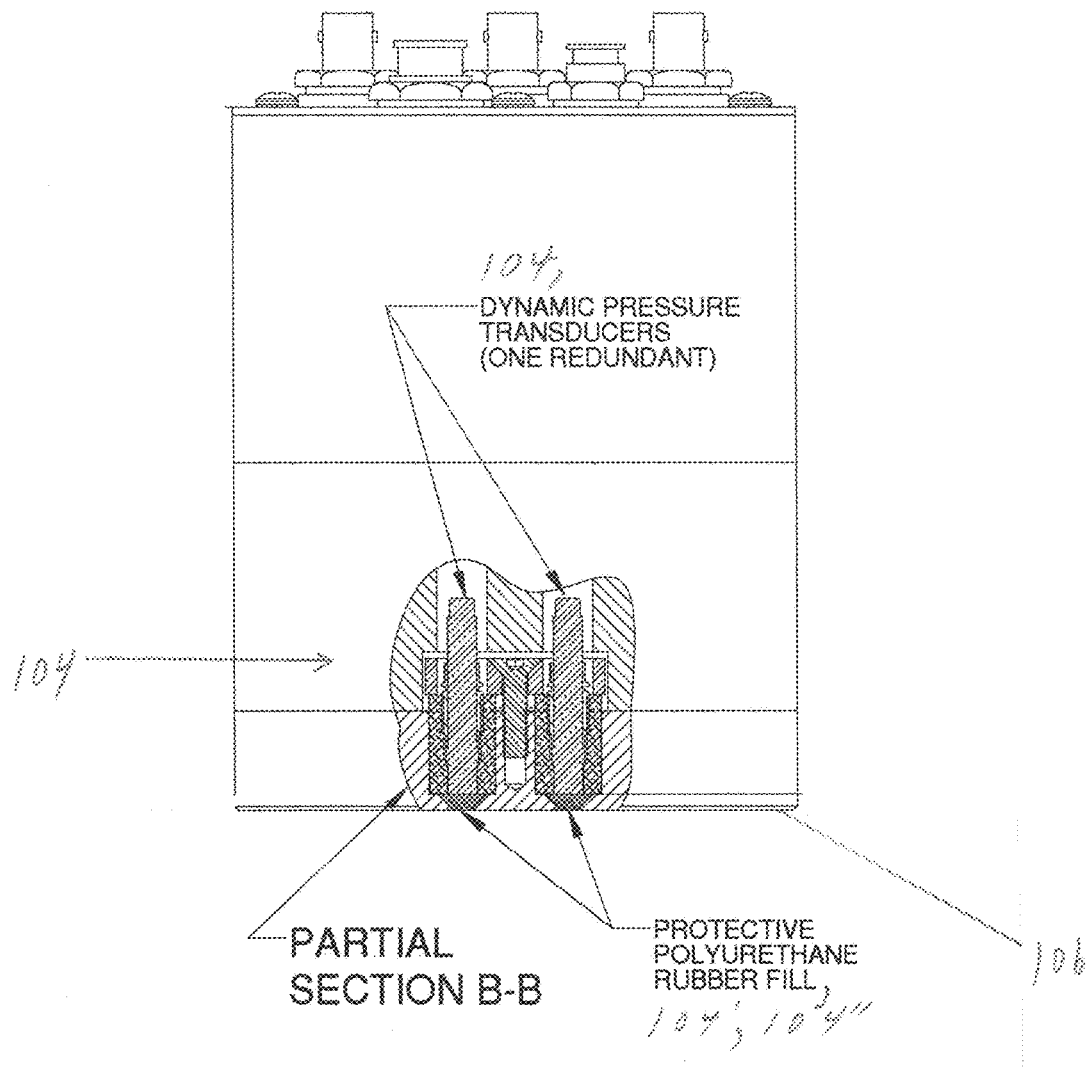
FIG. 1e is a sectional view of the end the acoustic probe shown in FIG. 1c along section lines B-B.

CCS-0075: FIGS. 1a-2b,

Real Time Air Measurement Applications in Wet Concrete

FIGS. 1a to 1e show the present invention in the form of apparatus generally indicated as 100 that may include an acoustic-based air probe like element 101. The acoustic-based air probe 101 may include an acoustic source generally indicated as 102 (see FIG. 1d) configured to provide an acoustic signal into a mixture of concrete; and an acoustic receiver generally indicated as 104 (see FIG. 1 e) configured to be substantially co-planar with the acoustic source 102, to respond to the acoustic signal, and to provide signaling containing information about the acoustic signal injected into the mixture of concrete. By way of example, the acoustic source 102 may consist of an arrangement of parts and components and is best shown in detail in FIG. 1d. By way of example, the acoustic receiver 104 may consist of at least an arrangement of one or more transducers and fills and is best shown in FIG. 1 e.

The acoustic-based air probe 101 may include a planar probing surface 106 having a first aperture 106a formed therein configured to receive part of the acoustic source 102, including a hardened steel piston 122, as best shown in FIG. 1 d. At the interface with the planar probing surface 106, the hardened steel piston 122 is surrounded by a circumferential channel 122a, so as not to be in physical contact with the planar probing surface 106. The planar probing surface 106 may include at least one second aperture 106b, 106c formed therein configured to receive at least one part 104', 104" of the acoustic receiver 104. The part 104', 104" are shown as a protective polyurethane rubber member in FIG. 1 e. The planar probing surface 106 may be configured as a hardened steel face plate, although the scope of the invention is intended to include using other type or kinds of materials either now known or later developed in the future. The acoustic receivers 104 are configured in relation to the center of the hardened steel piston 122 of the acoustic source 102 and defined by a radius R, as best shown in FIG. 1 c, so that the acoustic receivers 104 are arranged and configured substantially on the circumference of a circle defined by the radius R from the center of the hardened steel piston 122.

The acoustic receiver 104 may include, or take the form of, a dynamic pressure transducer, as best shown in FIG. 1 e.

In operation, and by way of example, the acoustic receiver 104 may be configured to receive acoustic signals, e.g., having a frequency in a range of about 100-500 Hz, including 330 Hz, although the scope of the invention is intended to include using other frequencies and other ranges either now known or later developed in the future.

By way of example, the acoustic source 102 may include, or take the form of, or be configured as, a floating mass, consistent with that shown in FIG. 1 d.

In FIG. 1 d, the acoustic source 102 is shown in the form of a piston module assembly 120 having the rigid hardened steel piston 122 configured with a channel 124 to receive, or be coupled to, a piston shaft 126. The acoustic-based air probe 101 has a base plate disk 125 that contains the piston module assembly 120, as well as other components in FIG. 1d. The rigid hardened steel piston 122 is enclosed, surrounded and configured to move in relation to a low durometer cast silicone rubber 123 and photo-etched flexures 127, so as to provide the floating mass aspect of the acoustic source 102. The low durometer cast silicone rubber 123 may also be configured to perform sealing functionality in relation to the mixture of the concrete. The acoustic source 102 may also include a vibration isolated actuator block assembly 128, best identified in FIG. 1 b, having a stationary voice coil actuator field assembly 130 in combination with a voice coil actuator field assembly 132 having an accelerometer transducer configuration. The vibration isolated actuator block assembly 128 may be configured to drive and vibrate the piston shaft 126, consistent with that shown in FIG. 1 d, so as to provide the acoustic signal to the mixture of the concrete when the acoustic-based air probe is inserted into the mixture. The apparatus 100 may also be configured with signal processing technology (not shown) for driving the acoustic source 102, as would be appreciated by a person skilled in the art.

The acoustic-based air probe 101 may include a fluid/media temperature sensor 134, consistent with that shown in FIG. 1 d, configured to provide a temperature reading of the mixture.

The acoustic-based air probe 101 may include a voice coil temperature sensor 136, consistent with that shown in FIG. 1 d, configured to provide a temperature reading of the stationary voice coil actuator field assembly 130.

The acoustic-based air probe 101 may include two acoustic receivers 104, 104', that may take the form of the two dynamic pressure transducers, consistent with that shown in FIG. 1 e.

The acoustic-based air probe 101 may include some combination of a connector/wiring cover plate 140, and various connectors configured in relation to the same, including a pressure sensor no. 1 connector 142 for providing the signaling in relation to one pressure sensor, a pressure sensor no. 2 connector 144 for providing the signaling in relation to the other pressure sensor, a voice coil drive connector 146 for providing the signaling in relation to the voice coil drive 130 (FIG. 1 d), a temperature sensor connector 148 for providing the signaling in relation to a temperature, and an accelerometer connector 150 for providing the signaling in relation to the voice coil actuator moving coil assembly 132 (FIG. 1d), all shown in FIG. 1 b.

Applications

Figure 2A:
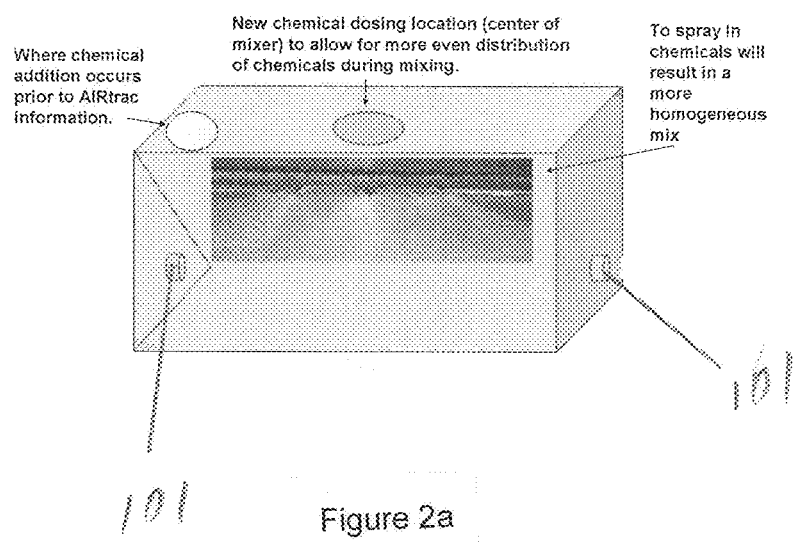
FIG. 2a is a diagram of a stationary mixer having a new dosing location in the center of the mixer to allow for an even distribution of chemicals during mixing, according to some embodiment of the present invention.

The apparatus 100 may include, or take the form of, a stationary mixer 20 having a wall 20a with the one or more acoustic-based air probes 101 arranged therein, including where the stationary mixer 20 is configured with a central chemical dosing location 20b to allow for more even distribution of chemicals into the mixing. In FIG. 2a, the acoustic-based air probe or measurement device 101 according to the present invention, is shown arranged in a precut hole 20c of the stationary mixer 20. Instrumenting the stationary mixer 20 with more than one air meter or acoustic-based air probe 101 (for example: one on the left side and one on the right side) will help in understanding the mixing efficiency and performance of a particular mixer. With this information different techniques may be implemented to improve homogeneity of the entire mixed batch. The addition of the admix chemicals made may need to be spread (sprayed) more evenly throughout the mixing area rather than streamed in one location. Or the more centralized dosing location 20b may also be an improvement on current methodology.

The apparatus 100 may also include dosing apparatus (not shown) configured to respond to the signaling, and provide a control signal to control the dosing of a chemical to be added or subtracted from the mixture, e.g., including to the dosing location 20a shown in FIG. 2a.

Figure 2B:
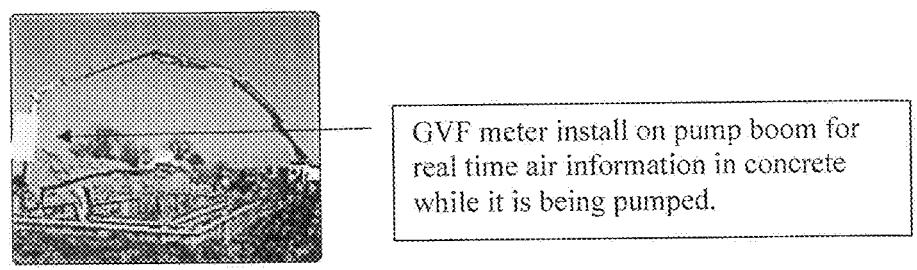
FIG. 2b is a diagram of a GVF meter installed on a pump boom for real time air information in concrete while it is being pumped, according to some embodiments of the present invention.

The apparatus 100 may include a concrete pump boom having a wall with the acoustic-based air probe arranged therein, consistent with that shown in FIG. 2b.

Precast Applications

Form Application—Forms used in a precast facility would benefit from being instrumented with entrained air measurement capability. This would enable a concrete producer to measure entrained air levels in concrete as the form is being filled. This will also give them an understanding of how much air is lost from the concrete mixer to placement into the form and will enable better planning to meet air specification. According to some embodiments of the present invention, the apparatus 100 may include, or take the form of, a precast form (not shown) having a wall with the acoustic-based air probe 101 arranged therein.

Ready Mix Applications

Pumping Application—Ready Mix Boom Pump—This application can utilize the known SONAR-based SOS GVF meter developed by the assignee of the instant patent application may also be used for real time entrained air information in the concrete as it is being pumped in order to control and understand air levels in wet concrete, which is very important. Too much air will effect strength and too little air will effect the durability (freeze/thaw) of the concrete. Since a great deal of ready mix concrete is pumped into place at job sites every day, it is important to know how the pumping of entrained air concrete can effect the air content in concrete. Once the air level in the concrete is understood at placement the appropriate adjustments can be made further upstream to compensate for the air loss during pumping. Theories concerning air losses within the concrete mix during pumping include: the large drop within the boom, high pressure within the pipes, pump configurations and attachments and the materials used in the concrete mix.

Ready Mix Stationary Central Mixer: The known SONAR-based SOS technology developed by the assignee of the instant patent application may also be used for real time air information in ready mix stationary central mixers. In many areas of the world (especially Europe), the wet batching process utilizes stationary mixers.

Ready Mix Truck Rotating Drum Mixer: The known SONAR-based SOS technology developed by the assignee of the instant patent application may also be used for ready mix truck rotating drum mixer or stationary mixers. The primary difference will be that this unit can be battery operated and will transmit the real time air data wirelessly. This information will enable every batch of ready mix concrete to arrive at the job site within air specification. According to some embodiments of the present invention, the apparatus 100 may include, or take the form of, a ready mix truck rotating drum mixer (not shown) having a wall with the acoustic-based air probe 101 arranged therein.

Air level will be monitored the entire travel time and can be adjusted if necessary by chemical addition.

Ready Mix Rotating Drum Central Mixer: These central mixers are very similar to the truck mixers, only usually a little larger. The rotating drum central mixers are usually 10-12 yards in size. Real time air information will allow for precise control of air before the batch is dumped into the truck.

Ready Mix Truck Chute Application: Ready mix truck delivery chute for real time air information. This would be mounted in such a way that an air measurement would be made as the concrete passes over it as it exits the truck. According to some embodiments of the present invention, the apparatus 100 may include, or take the form of, a ready mix truck chute (not shown) having a wall with the acoustic-based air probe 101 arranged therein.

Form Application, including Ready Mix Forms: This application may take the form of a disposable devise that could make an air measurement of the wet concrete after the form is filled.

FIGS. 3a to 3d

Handheld Unit or Acoustic-based Air Probe

FIGS. 3a to 3d show the present invention as apparatus in the form of a handheld unit or acoustic-based air probe 50, according to some embodiments of the present invention. The acoustic-based air probe 50 may be configured with a probe portion 52 and a handle portion 54. The handheld unit or acoustic probe 50 can be used both in precast and ready mix once concrete is poured into any form. The probe portion 52 of the handheld unit 50 may be submerged or dipped into the concrete, a noise source activated therein and sound speed measurement made, consistent with that disclosed herein. This technique may potentially take the place of, or augment or compliment, a known Type B pressure pod currently utilized in and by the industry.

The probe portion 52 may be configured with an acoustic source 56 configured to provide an acoustic signal injected into a mixture of concrete; and an acoustic receiver 58 configured to respond to the acoustic signal, and provide signaling containing information about the acoustic signal injected into the mixture of concrete. In FIG. 3d, the acoustic source 56 is shown in the form of a piston acoustic source, and the acoustic receiver 58 is shown in the form of a dynamic pressure transducer, although the scope of the invention is intended to include other types or kind of acoustic sources and acoustic receivers either now known or later developed in the future.

The probe portion 52 may also be configured with at least one spacer strut 60 configured to connect one member 62 of the probe portion 52 having the acoustic source 56 to the other member 64 of the probe portion 52 having the acoustic receiver, so as to form a space in-between configured for receiving a portion of the mixture of the concrete when first and second members 62, 64 of the probe portion 52 are dipped into the mixture of concrete and the acoustic signal is transmitted through the mixture. The at least one spacer strut 60 may include three spacer struts that are triangularly arranged and equally-spaced to connect the acoustic source and acoustic receiver so as to form the space in-between, as shown in FIGS. 3c and 3d, although the scope of the invention is intended to include using one strut, two struts, four struts, etc. The scope of the invention is not intended to be limited to the number of strut(s) being used, or the physical arrangement of the struts in relation to one another. The at least one spacer strut 60 may be configured with a wiring channel 60a for providing a wire from the acoustic receiver 58, as best shown in FIG. 3c.

The member 64 of the probe portion 52 may include a sealed end cap assembly 60a configured to contain the acoustic receiver in a sealing manner. The member 62 of the probe portion 52 may include a sealed assembly 62a configured to contain the acoustic source 56 in a sealing manner. The sealed assembly 62a may include a vibration isolated actuator block 62b configured to actuate the piston acoustic source 56. The vibration isolated actuator block 62b may include a voice coil actuator moving coil assembly 62c with an accelerometer transducer and a stationary voice coil actuator field assembly 62d. The sealed assembly 62a may include hemisphere vibration mounts 60e configured between an alignment cap 60f and the vibration isolated actuator block 62b and also configured between the vibration isolated actuator block 62b and the acoustic source 56, as best shown in FIG. 3d. The sealed assembly 62a may include a spring seal 62g, including a cast urethane spring seal, configured between the acoustic source 56 and an acoustic source retaining member 62h, and a photo-etched flexure 62i configured between the acoustic source 56 and the acoustic source retaining member 62h.

The member 62 of the probe portion 52 may include a second acoustic receiver 60j configured to respond to the acoustic signal, and provide further signaling containing information about the acoustic signal injected into the mixture of concrete. The second acoustic receiver 60j may be configured on the sealed assembly 62a so as to receive the acoustic signal that is reflected from the mixture of concrete. In contrast, the acoustic receiver 58 may be configured so as to receive the acoustic signal that is transmitted directly through the mixture of concrete.

The sealed assembly may also include a temperature sensor 60k configured to respond to the temperature of the mixture.

Figure 3A:
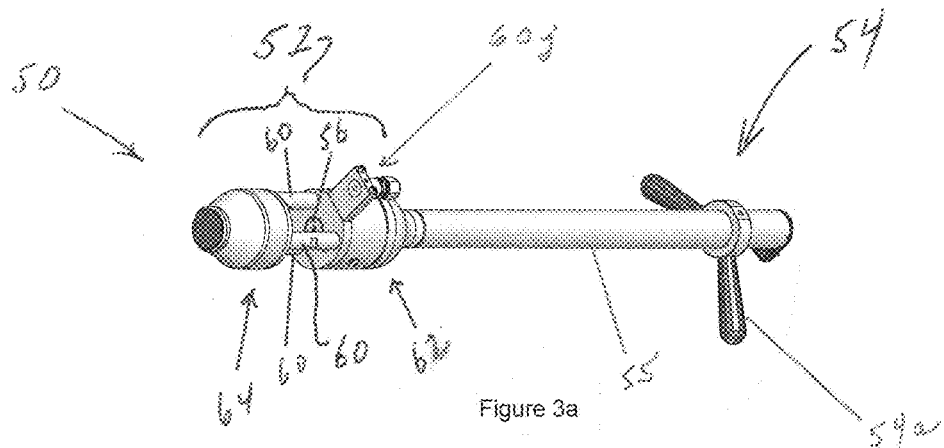
FIG. 3a is a diagram of a handheld acoustic probe, according to some embodiments of the present invention.
Figure 3B:
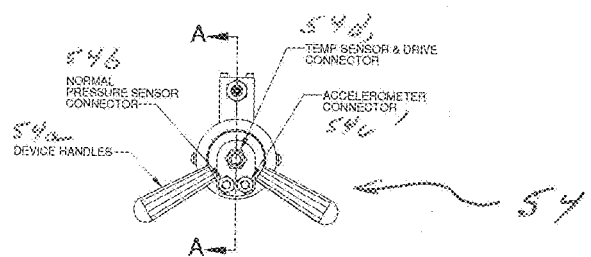
FIG. 3b is an axial view of the handheld acoustic probe shown in FIG. 3a, according to some embodiments of the present invention.
Figure 3C:
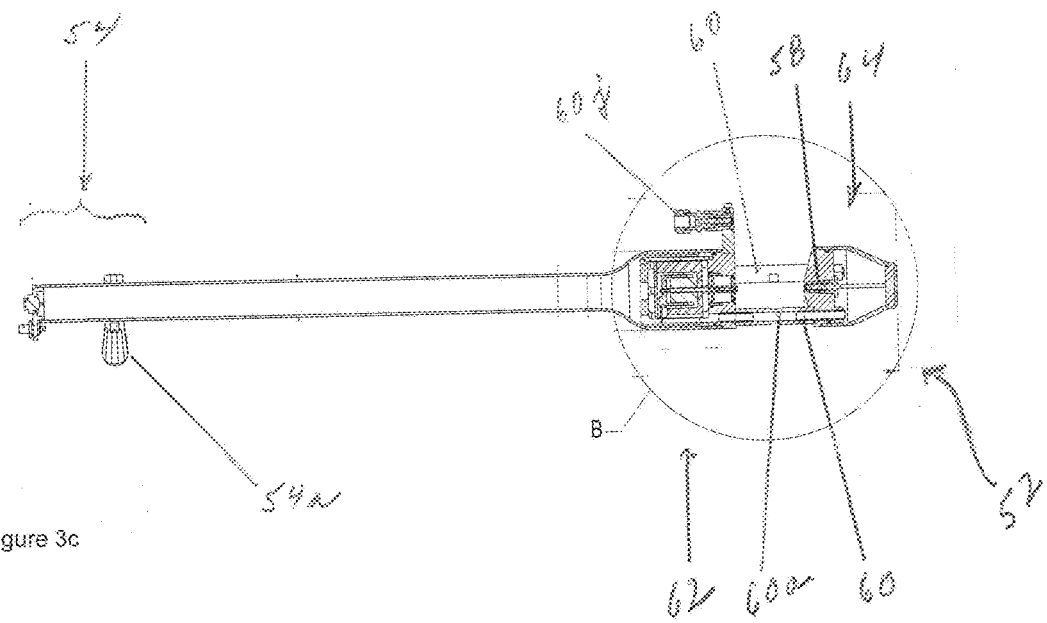
FIG. 3c is a cross-sectional view of the handheld acoustic probe shown in FIG. 3b along section lines A-A, according to some embodiments of the present invention.
Figure 3D:
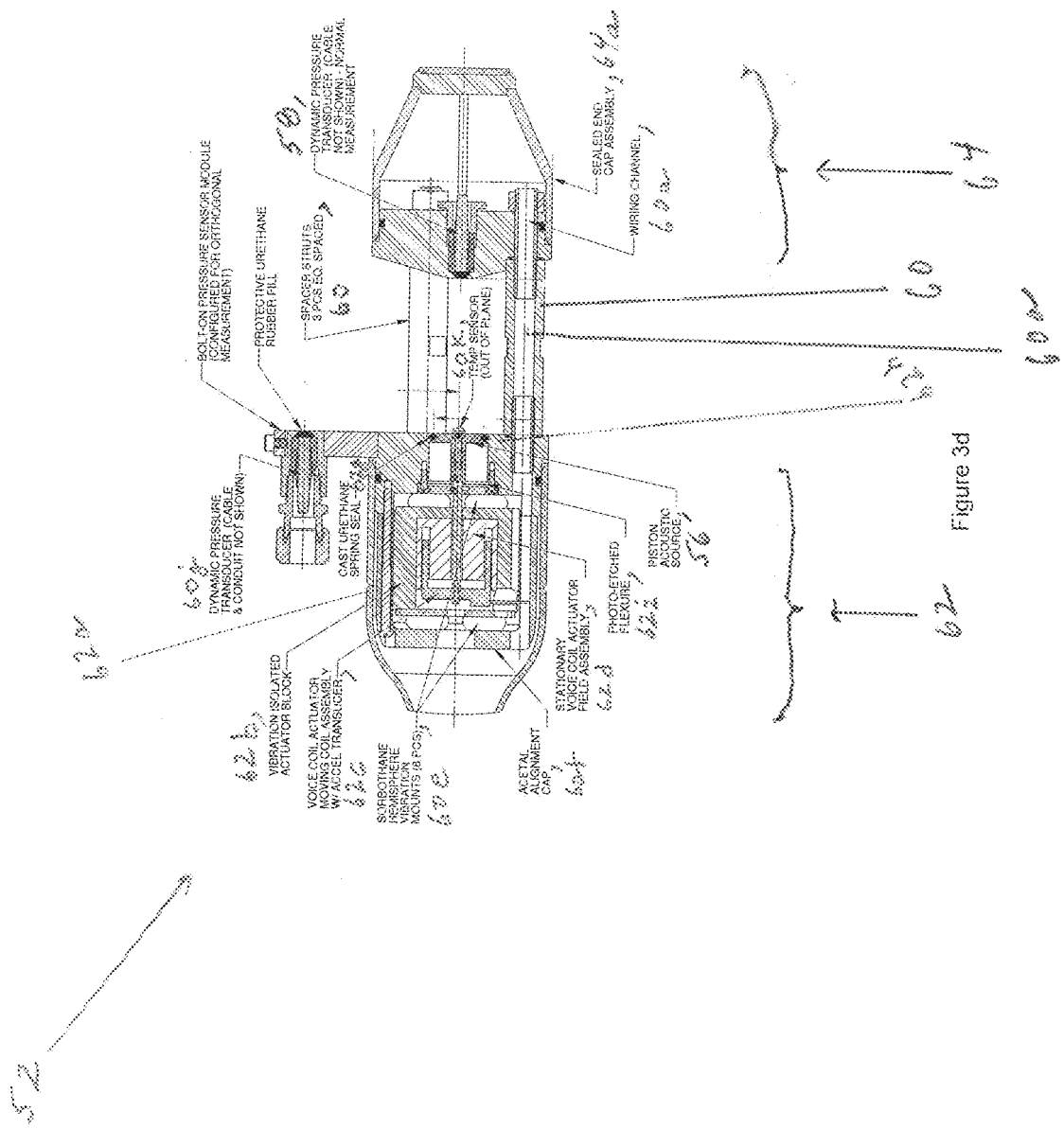
FIG. 3d is an enlarged view of a part of the handheld acoustic probe shown in FIG. 3c and labeled B, according to some embodiments of the present invention.

The handle portion 54 on the other end of the handheld acoustic-based air probe may be configured with some combination of device handles 54a, a normal pressure sensor connector 54b, an accelerometer connector 54c and a temperature and drive connector 54d, as best shown in FIGS. 3a and 3b.

According to some embodiments, the handheld acoustic-based air probe 50 may include a signal processor configured to perform the signal processing functionality consistent with that disclosed herein.

By way of example, the signal processor may be configured to determine the measurement of air percentage in the mixture of concrete based at least partly on using other types or kinds of SONAR-based techniques either now known or later developed in the future, according to some embodiments of the present invention, and consistent with that disclosed herein.

Alternatively, the signal processor may be configured to receive signaling containing information about an acoustic signal injected into a mixture of concrete, e.g., from the acoustic receiver 58 (see FIG. 3c); and determine a measurement of air percentage in the mixture of concrete based at least partly on a dual frequency technique that depends on a relationship between the acoustic signal injected, e.g., by the acoustic source 56, and the signaling received, according to some embodiments of the present invention, and consistent with that disclosed herein.

Alternatively, the acoustic signal injected may be a reference signal; the signaling received may be detected signaling; and the signal processor may be configured to determine the measurement of air percentage in the mixture of concrete based at least partly on mixing the reference signal with the detected signaling using a phase sensitive lock-in approach, according to some embodiments of the present invention, and consistent with that disclosed herein.

Alternatively, the signal processor may be configured to determine the measurement of air percentage in the mixture of concrete based at least partly on correlating the acoustic signal injected and the signaling received, according to some embodiments of the present invention, and consistent with that disclosed herein.

The scope of the invention is intended to be limited to the way or technique that the signal processor in the handheld acoustic-based air probe determines the measurement of air percentage in the mixture of concrete. By way of example, the signal processor may be configured or arranged in an intermediate portion 55 of the handheld unit 50, although the scope of the invention is intended to include configuring the signal processor somewhere else in the probe 50.

According to some embodiments, the handheld acoustic-based air probe 50 may provide the signaling containing information about an acoustic signal injected into a mixture of concrete, e.g., from the acoustic receiver 58, to a signal processor that is external to, and does not form part of, the handheld acoustic-based air probe 50, which determines the measurement of air percentage in the mixture of concrete based at least partly on one or more of the signal processing techniques disclosed herein.

So as not to clutter up FIGS. 3a to 3d, each Figures does not include every reference numeral used to identify every elements shown therein.

Moreover, according to some embodiments of the present invention, the known type B canister in the art or another shaped canister may be configured or instrumented with speed of sound measurement capability. This would be a sampling method that would enable an air measurement within seconds rather than minutes.

CCS-0067 and 0104, FIG. 4

The Signal Processor of Dual Frequency Techniques

FIG. 4 shows apparatus generally indicated as 10 according to some embodiments of the present invention. The apparatus 10 may include a signal processor 10a that receives signaling containing information about an acoustic signal injected into a mixture of concrete; and determines a measurement of air percentage in the mixture of concrete based at least partly on a dual frequency technique that depends on a relationship between the acoustic signal injected and the signaling received.

By way of example, and consistent with that described herein, the functionality of the signal processor 10a may be implemented using hardware, software, firmware, or a combination thereof, although the scope of the invention is not intended to be limited to any particular embodiment thereof. In a typical software implementation, the signal processor would be one or more microprocessor-based architectures having a microprocessor, a random access memory (RAM), a read only memory (ROM), input/output devices and control, data and address buses connecting the same. A person skilled in the art would be able to program such a microprocessor-based implementation to perform the functionality set forth in the signal processing block 10a, such as determining the gas volume fraction of the aerated fluid based at least partly on the speed of sound measurement of the acoustic signal that travels through the aerated fluid in the container, as well as other functionality described herein without undue experimentation. The scope of the invention is not intended to be limited to any particular implementation using technology now known or later developed in the future. Moreover, the scope of the invention is intended to include the signal processor being a stand alone module, as shown, or in the combination with other circuitry for implementing another module.

It is also understood that the apparatus 10 may include one or more other modules, components, circuits, or circuitry 10b for implementing other functionality associated with the apparatus that does not form part of the underlying invention, and thus is not described in detail herein. By way of example, the one or more other modules, components, circuits, or circuitry 10b may include random access memory, read only memory, input/output circuitry and data and address buses for use in relation to implementing the signal processing functionality of the signal processor 10a, or devices or components related to mixing or pouring concrete in a ready-mix concrete truck or adding chemical additives, etc.

Figure 5A:
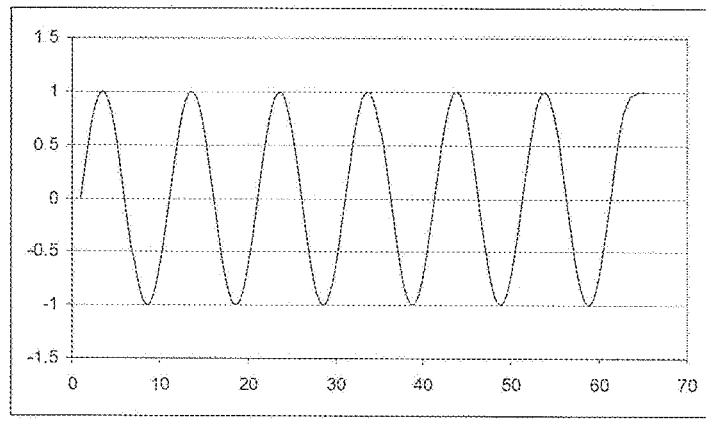
FIG. 5a is a graph of a single frequency being injected into a mixture of concrete, according to some embodiment of the present invention.
Figure 5B:
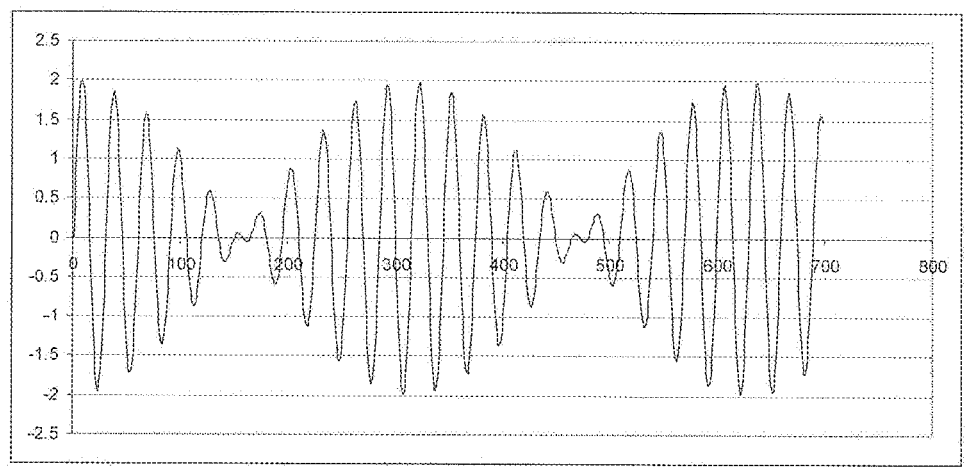
FIG. 5b is a graph of two frequencies having a frequency difference being injected into a mixture of concrete, according to some embodiment of the present invention.

Consistent with that set forth in relation to FIGS. 5a-5b, the acoustic signal injected may be a reference signal; the signaling received may be detected signaling; and the signal processor may be configured to determine the measurement of air percentage in the mixture of concrete based at least partly on mixing the reference signal with the detected signaling using a phase sensitive lock-in approach.

Figure 6A:
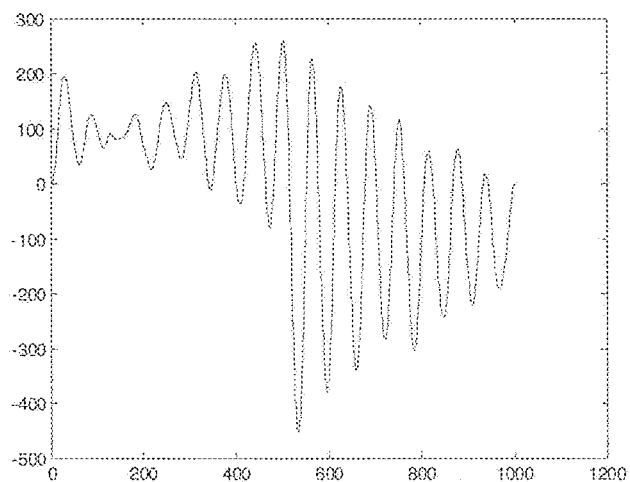
FIG. 6a is a graph of an example of a correlation function if there is strong system noise present and some of that noise coincides with a frequency of actuation.
Figure 6B:
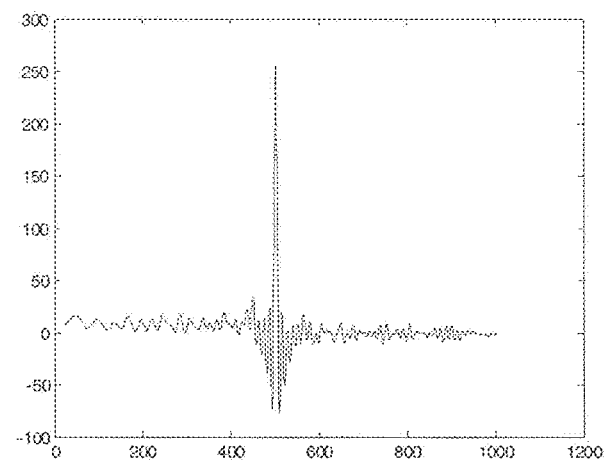
FIG. 6b is a graph of an example of a correlation function if there is strong system noise present and a sweep of the excitation frequency is provided to an actuator.
Figure 6C:
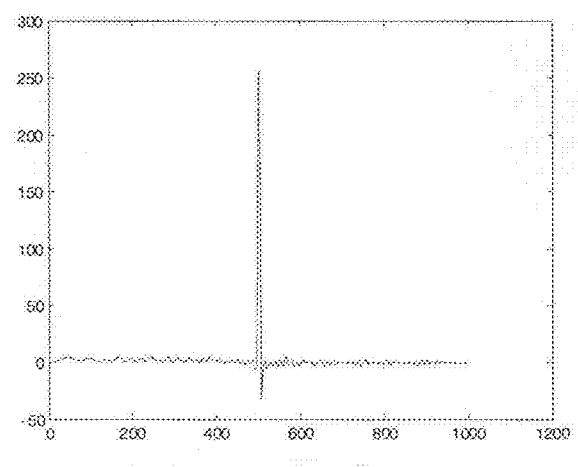
FIG. 6c is a graph of an example of a further correlation function when a PRBS encoded oscillation is used in the presence of a large noise system. provided to an actuator.

Alternatively, consistent with that set forth in relation to FIGS. 6a to 6c, the signal processor may be configured to determine the measurement of air percentage in the mixture of concrete based at least partly on correlating the acoustic signal injected and the signaling received.

CCS-0067: FIGS. 5a-5b,

Phase Sensitive Dual Frequency Lock-in Measurement for Concrete Air Content with Quality Factor One approach to the measurement of air percentage in concrete is to measure the speed of sound (SOS) in the mixture and then through the use of the Wood's equation to calculate the amount of gas present. Various acoustic speed of sound measurements used in relation to SONAR-based technology as well as other sound receiving technology are set forth below with numerous patents disclosing this technology. This measurement of air percentage in concrete can be very difficult in materials like concrete where acoustic waves will quickly die out in strength due to the material's constituents along with other factors. This can be overcome by injecting a strong acoustic signal into the mixture at one point and then timing the signal propagation through a representative section of the material. However, this approach requires significant amounts of energy to produce a large compression wave in the concrete.

According to some embodiments of the present invention, a variation of this approach may be implemented that would require a modest acoustic signal to be injected but a very sensitive detection technique that can pull the injected signal out of the other acoustic "noise" that is present in the system. One detection technique that is well suited for this is a phase sensitive lock-in approach.

In a lock-in approach, a reference signal may be injected into the mixture and that same signal may be mixed with a resultant detected signal from the mixture. After a low pass filter is used to get the DC component of the result, a value may be obtained that is proportional to the amplitude and phase of the detected signal at the reference frequency. If the same calculation is made with the reference shifted by 90 deg, the phase and amplitude components can be separately determined. If one takes $\Theta_{ref}$ as the reference phase, $\Theta_{det}$ as the detected phase, $A_{det}$ as the detected signal amplitude at the frequency of interest, then the signal amplitude and the signal phase difference may be determined using the following set of equations:

$$\Theta = \Theta_{det} - \Theta_{ref},$$

$$X \sim A_{det} \cos(\Theta),$$

$$Y \sim A_{det} \cos(\Theta + 90 \deg) = A_{det} \sin(\Theta),$$

Signal amplitude=$A\text{det}=(X^2*Y^2)^{1/2}$, and

Signal phase difference=$\ominus=\tan^{-1}(Y/X)$.

The signal phase difference calculated along with the frequency can then be used to determine the time of propagation of the signal in the material and then the SOS.

Ambiguity in the Detected Acoustic Signal

However, an ambiguity exists once the detected signal has gone though a propagation time equal to 2*pi of the injected signal (or any multiple). This can be somewhat prevented by assuring that the frequency used for injection is low enough that the time delay can not introduce the ambiguity, however this will severely restrict the operational range of the measurement. Variations in the air content along with the attenuation characteristic of the materials may force the system to operate in a region where the ambiguity will exist. This can be prevented by injecting two slightly different frequencies into the material and then detecting each to determine the relative phase between the two injected signals, e.g., using the acoustic probe shown in FIGS. 1a to 1e that include two dynamic transducers shown in FIG. 1e. An ambiguity can still exist but it will be a function of the difference of the two injected signals rather than just the single injected frequency. This can be seen through the illustrations in FIGS. 5a and 5b. In FIG. 5a, the period of the single frequency is seen to be about 10 counts, this is the "distance" that can be measured with this system without ambiguity. In FIG. 5b, where there are 2 signals at a 10% frequency difference, now the overriding "beat" frequency determines the point at which the distance becomes ambiguous. This can be seen at about 325 counts, a very large extension of the range of the system.

An additional issue with a system such as this which calculates a SOS is the reliability of the calculation. The lock-in scheme above will always give a number for the phase delay and therefore the SOS but an indication or quality factor is needed to be able to gauge the reliability of that calculation. Since from the phase calculation the amplitude of the signal may also be obtained, this can be used for calculation of a quality metric. If one takes the amplitude of the signal at the injected frequency and compares that to several amplitudes of signals around that frequency, then one can get an indication of how the signal of interest is, or relates, to the surrounding "noise". If one takes the amplitude of the signal of interest at Asig and also take a sample of four other signals spaced adjacent to the original of A0, A1, A2 and A3, then one can average the four comparison signals and consider this the adjacent noise Anoise=(A0+A1+A2+A3)/4. A difference over sum normalization will give one a quality signal, Q, that varies between −1 to 1. With 1 representing a good quality, a 0 indicating same signal strength at frequency of interest as other frequencies and a −1 as a very weak signal of interest.

$Q=(A\text{sig}-A\text{noise})/(A\text{sig}+A\text{noise})$.

CCS-104: FIGS. 6a-6c,

Additional Concrete and Free Space Acoustic Measurement Techniques to Improve Signal Range and Signal to Noise The present invention, according to some embodiments, also provides further techniques that builds upon the aforementioned disclosure describing the dual frequency method for extending the unambiguous range as well as the sensitivity of the concrete (free-space acoustics) signal detection. As mentioned, several techniques in addition to the lock-in approach that can be utilized for increasing the sensitivity and accuracy of the speed of sound detection beyond the current single wave correlation techniques.

If one takes a look at the basic technique, a single frequency acoustic wave is introduced into the mixture to be measured by way of an actuator. A detector is situated a known distance away and it will detect the introduced acoustic wave along with all the background acoustic noise in the system. In many situations the background acoustic noise can be much larger than the actuated signal making detection very difficult. However, by correlating the detected signal with the actuated signal any phase delay due to the transit time of the acoustic wave in the material can be determined and the subsequent speed of sound can be calculated. Using the correlation helps to detect only the signal of interest and works well provided that the system noise is not too overwhelmingly strong and does not have significant frequency content at the actuation frequency. FIG. 6a shows what the correlation function could look like if there is strong system noise present and some of that noise coincides with the frequency of the actuation.

One way to mitigate the distortion and errors associated with the system noise is to utilize several frequencies in the excitation. The dual frequency lock-in technique provided benefits related to dual frequency excitation, but this concept can be extended even further to the use of a continuum of frequencies. A simple sweep of the excitation frequency fed to the actuator can greatly increase the sensitivity of the correlation process by reducing the effects of the system noise and specifically reduce the degradation caused by system acoustic tones that may be present. Such a sweep can be described by:

$Y(i)=A \sin(ai^2/2+bi)$.

The same correlation processing can be utilized with the frequency sweep, FIG. 6b shows a correlation function obtained with strong system noise present.

Additional techniques such as encoded pulsing can be used to alternatively enhance the signal-to-noise of the detected acoustic signal. One such encoding is through the use of a pseudo-random sequence (PRBS). A PRBS is defined as a sequence of N bits where the autocorrelation of the sequence gives a number proportional to the number of on bits times the sequence length when there is 0 misalignment and a low number proportional to only the number of on bits when misaligned. This property makes it particularly suitable for use when a correlation is used to detect a low level signal. Due to the random nature of the signal encoding the probability that system acoustic noise will mimic the encoded signal is practically nil and a very strong correlation will be seen. FIG. 6c shows the further improved correlation function when a PRBS encoded oscillation is used in the presence of large system noise.

As can be seen with the encoded techniques a very good signal-to-noise can be achieved.

In the case of free-space acoustic measurements, the PRBS excitation can be created in a variety of ways such as turning on and off the excitation acoustic wave according to the PRBS sequence, or by frequency modulating the acoustic signal by the PRBS sequence. Other types of frequency encoding can be utilized such as m-sequence codes or frequency shift keying approaches.

The SONAR-based Technology

The new techniques for impact and coherent noise sources for acoustic speed of sound measurements, including such acoustic speed of sound measurements used in relation to SONAR-based technology as well as other sound receiving technology as shown and described herein. By way of example, the SONAR-based entrained air meter may take the form of SONAR-based meter and metering technology disclosed, e.g., in whole or in part, in U.S. Pat. Nos. 7,165,464; 7,134,320; 7,363,800; 7,367,240; and 7,343,820, all of which are incorporated by reference in their entirety.

A. Introduction

The known SONAR-based technology includes a gas volume fraction meter (known in the industry as a GVF-100 meter) that directly measures the low-frequency sonic speed (SOS) of the liquid or slurry flowing through a pipe. By way of example, the SONAR-based entrained air meter may take the form of SONAR-based meter and metering technology disclosed, e.g., in whole or in part, in U.S. Pat. Nos. 7,165,464; 7,134,320; 7,363,800; 7,367,240; and 7,343,820, all of which are incorporated by reference in their entirety. Using the Wood's equation, the volume percent of any gas bubbles or the gas void fraction (GVF) is determined from the measured SOS. The Wood's equation requires several other inputs in addition to the measured SOS of liquid/gas mixture. One of the additional inputs in particular, the static pressure of the liquid/gas mixture, can be very important for an accurate calculation of the GVF. To a first order, if the static pressure used for the GVF calculation differs from the actual static pressure of the liquid/gas mixture, then the calculated GVF may typically differ from the actual GVF by 1% as well. For example:

Static Pressure used for GVF calculation=20 psia

Calculated GVF=2%

Actual Static Pressure=22 psia

Static pressure error=22/20−1=0.1=10%

Actual GVF=2%×(1+0.1)=2.2% (10% error)

In many cases, the static pressure of the liquid/gas mixture is available through existing process plant instrumentation. In this case, the measured static pressure can be input directly to the GVF calculation through, e.g., an analog 4-20 mA input in the SONAR-based gas volume fraction transmitter (e.g. GVF-100 meter). Alternatively, a correction to the calculated GVF can be made in the customer DCS for any variation from the fixed pressure that was used to originally calculate the GVF.

In other cases, a static pressure transmitter can be added to the process plant specifically to measure the static pressure used for the GVF calculation. The measured pressure can either be input to the SONAR-based gas volume fraction transmitter (e.g., GVF-1200) or correction made in the DCS as described above.

Occasionally, a the SONAR-based gas volume fraction meter (e.g., GVF-100) may be installed at a location in the process that does not already have a static pressure gauge installed and it is impractical to add one. This could be a location where there is no existing penetration of the pipe to sense the pressure and it would be difficult or expensive to add one. In the case, where a traditional pressure gauge is not available and it is desirable to have a static pressure measurement the following description of a non-intrusive (clamp on) static pressure measurement could be used.

B. Description

For example, according to some embodiments of the present invention, a non-intrusive static pressure measurement may be sensed using traditional strain gauges integrated into the sensor band of the SONAR-based gas volume fraction sensing technology (e.g. the known GVF-100 meter). As the static pressure inside the pipe changes, the static strain on the outside of the pipe also changes. Using a thin-wall assumption for simplicity (t/R<10, where t is the wall thickness and R is the radius) the tangential strain due to internal static pressure is:

$$\varepsilon = \frac{pR}{Et},$$

where ε is the tangential strain (inch/inch), R is the radius (inch), E is the modulus of elasticity (lb/in2) and t is the wall thickness (inch). The radius, wall thickness and modulus is generally known, or at least constant and so if the tangential strain is measured the internal static pressure can be determined.

By way of example, according to one embodiment of the present invention, four strain gauges could be arranged on the sensor band of the SONAR-based gas volume fraction sensing technology (e.g. the known GVF-100 meter) in a Wheatstone bridge configuration to maximize strain sensitivity and minimize temperature effects. In this case, the sensitivity assuming a strain gauge factor of 2, the sensitivity is approximately 13 µV/µε, where V is volts. Assuming a 4-inch schedule 40 carbon steel pipe, a one psi change in pressure would cause a 4 µV change in Wheatstone bridge output. This sensitivity would increase for larger diameter pipes which generally have a smaller t/R.

The integrated pressure gauge could be calibrated in-situ for best accuracy, but it may be sufficient to normalize the pressure output to a certain known state then use the tangential strain formula above with known pipe parameters to calculate the pressure from the measured strain.

The SONAR-based entrained air meter and metering technology are known in the art and may take the form of a SONAR-based meter disclosed, e.g., in whole or in part in U.S. Pat. Nos. 7,165,464; 7,134,320; 7,363,800; 7,367,240; and 7,343,820, all of which are incorporated by reference in their entirety. The SONAR-based entrained air meter and metering technology is capable of providing a variety of information, including the pure phase density and pure phase liquid sound speed is known, such that the GVF can be determined by measuring the speed of sound and then applying the Woods Equation.

Determining the GVF by measuring the speed of sound can provide fast an accurate data. Also the SOS measurement system can be very flexible and can easily be configured to work with different concrete containers and sample particular volumes.

Consistent with that described above, the SONAR-based entrained air meter and metering technology are known in the art and may take the form of a SONAR-based meter disclosed, e.g., in whole or in part in U.S. Pat. Nos. 7,165,464; 7,134,320; 7,363,800; 7,367,240; and 7,343,820.

Other Known Technology

The acoustic transmitter, the acoustic receiver or receiver probe and/or transponders are devices that are known in the art, and the scope of the invention is not intended to be limited to any particular type or kind either now known or later developed in the future.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. Apparatus comprising:
a handheld acoustic-based air probe configured with
an acoustic source configured to provide an acoustic signal injected into a mixture of concrete; and
an acoustic receiver configured to respond to the acoustic signal, and provide signaling containing information about the acoustic signal injected into the mixture of concrete;
wherein the handheld acoustic-based air probe comprises at least one spacer struts configured to connect a first member of the handheld acoustic-based air probe having the acoustic source to a second member of the handheld acoustic-based air probe having the acoustic receiver, so as to form a space in-between configured for receiving a portion of the mixture of the concrete when first and second members of the handheld acoustic-based air probe are dipped into the mixture of concrete and the acoustic signal is transmitted through the mixture.

2. Apparatus according to claim 1, wherein the handheld acoustic-based air probe comprises a sealed assembly configured to contain the acoustic source in a sealing manner.

3. Apparatus according to claim 2, wherein the vibration isolated actuator block comprises a voice coil actuator moving coil assembly with an accelerometer transducer and a stationary voice coil actuator field assembly.

4. Apparatus according to claim 2, wherein the sealed assembly comprises hemisphere vibration mounts configured between an alignment cap and the vibration isolated actuator block and also configured between the vibration isolated actuator block and the acoustic source.

5. Apparatus according to claim 2, wherein the sealed assembly comprises a spring seal, including a cast urethane spring seal, configured between the acoustic source and an acoustic source retaining member, and a photo-etched flexure configured between the acoustic source and the acoustic source retaining member.

6. Apparatus according to claim 2, wherein the sealed assembly comprises a temperature sensor configured to respond to the temperature of the mixture.

7. Apparatus according to claim 1, wherein the apparatus comprises a signal processor configured to
receive the signaling containing information about the acoustic signal injected into the mixture of concrete; and
determine the measurement of air percentage in the mixture of concrete based at least partly on a dual frequency technique that depends on the relationship between the acoustic signal injected and the signaling received.

8. Apparatus according to claim 7, wherein the dual frequency technique includes, or takes the form of, the signal processor being configured to determine the measurement of air percentage in the mixture of concrete based at least partly on mixing a reference signal with a detected signaling using a phase sensitive lock-in approach.

9. Apparatus according to claim 7, wherein the dual frequency technique includes, or takes the form of, the signal processor being configured to determine the measurement of air percentage in the mixture of concrete based at least partly on correlating the acoustic signal injected and the signaling received.

10. Apparatus according to claim 9, wherein the signal processor is configured to determine a time of propagation of the reference signal in the mixture of concrete and then a speed of sound measurement, based at least partly on the signal phase difference determined along with the frequency.

11. Apparatus according to claim 1, wherein the handheld acoustic-based air probe comprises a second acoustic receiver configured to respond to the acoustic signal, and provide further signaling containing information about the acoustic signal injected into the mixture of concrete.

12. Apparatus according to claim 11, wherein the second acoustic receiver is configured on the sealed assembly so as to receive the acoustic signal that is reflected from the mixture of concrete.

13. Apparatus according to claim 1, wherein the acoustic source and the acoustic receiver are configured on one end of the handheld acoustic-based air probe.

14. Apparatus according to claim 13, wherein the handheld acoustic-based air probe comprises another end configured with some combination of device handles, a normal pressure sensor connector, an accelerometer connector and a temperature and drive connector.

15. Apparatus according to claim 1, wherein the at least one spacer struts comprises three spacer struts that are triangularly arranged and equally-spaced to connect the acoustic source and acoustic receiver so as to form the space in-between.

16. Apparatus according to claim 1, wherein the at least one spacer struts comprises a wiring channel for providing a wire from the acoustic receiver.

17. Apparatus according to claim 1, wherein the handheld acoustic-based air probe comprises a sealed end cap assembly configured to contain the acoustic receiver in a sealing manner.

18. Apparatus according to claim 1, wherein the apparatus comprises a signal processor configured to
receive the signaling containing information about the acoustic signal injected into the mixture of concrete; and
determine a gas volume fraction of the mixture of concrete based at least partly on a speed of sound measurement of the acoustic signal that travels through the mixture, using a SONAR-based technique.

19. Apparatus comprising:
an acoustic-based air probe having;
an acoustic source configured to provide an acoustic signal into a mixture of concrete; and
an acoustic receiver configured to be substantially co-planar with the acoustic source, to respond to the acoustic signal, and to provide signaling containing information about the acoustic signal injected into the mixture of concrete;
wherein the acoustic source comprises a floating mass.

20. Apparatus according to claim 19, wherein the acoustic-based air probe comprises a planar probing surface having a first aperture formed therein configured to receive part of the acoustic source.

21. Apparatus according to claim 20, wherein the planar probing surface has at least one second aperture formed therein configured to receive part of the acoustic receiver.

22. Apparatus according to claim 20 or 21, wherein the planar probing surface is configured as a hardened steel face plate.

23. Apparatus according to claim 19, wherein the acoustic source comprises a piston module assembly having a rigid hardened steel piston configured to be coupled to a piston shaft.

24. Apparatus according to claim 23, wherein the acoustic-based air probe comprises a vibration isolated actuator block assembly having a stationary voice coil actuator field assembly in combination with a voice coil actuator field assembly having an accelerometer transducer, the vibration isolated actuator block assembly being configured to drive the piston shaft.

25. Apparatus according to claim 19, wherein the apparatus comprises dosing apparatus configured to respond to the signaling, and provide a control signal to control the dosing of a chemical to be added or subtracted from the mixture.

26. Apparatus according to claim 19, wherein the apparatus comprises a stationary mixer having a wall with the acoustic-based air probe arranged therein, including where the stationary mixer is configured with a central chemical dosing location to allow for an even distribution of chemicals into the mixing.

27. Apparatus according to claim 19, wherein the apparatus comprises a concrete pump boom having a wall with the acoustic-based air probe arranged therein.

28. Apparatus according to claim 19, wherein the apparatus comprises a precast form having a wall with the acoustic-based air probe arranged therein.

29. Apparatus according to claim 19, wherein the apparatus comprises a ready mix truck rotating drum mixer having a wall with the acoustic-based air probe arranged therein.

30. Apparatus according to claim 19, wherein the apparatus comprises a ready mix truck chute having a wall with the acoustic-based air probe arranged therein.

31. Apparatus according to claim 19, wherein the acoustic-based air probe comprises a protective polyurethane rubber member arranged in the at least one second aperture.

32. Apparatus according to claim 19, wherein the acoustic receiver comprises a dynamic pressure transducer.

33. Apparatus according to claim 19, wherein the acoustic receiver is configured to receive acoustic signals having a frequency in a range of about 100-500 Hz, including 330 Hz.

34. Apparatus comprising:
an acoustic-based air probe having:
an acoustic source configured to provide an acoustic signal into a mixture of concrete; and
an acoustic receiver configured to be substantially co-planar with the acoustic source, to respond to the acoustic signal, and to provide signaling containing information about the acoustic signal injected into the mixture of concrete;
wherein the apparatus forms part of a handheld device, having the acoustic-based air probe on one end and a handle on the other end.

35. Apparatus according to claim 34, wherein the acoustic-based air probe comprises a planar probing surface having a first aperture formed therein configured to receive part of the acoustic source.

36. Apparatus according to claim 35, wherein the planar probing surface has at least one second aperture formed therein configured to receive part of the acoustic receiver.

37. Apparatus according to claim 35 or 36, wherein the planar probing surface is configured as a hardened steel face plate.

38. Apparatus according to claim 34, wherein the apparatus comprises a signal processor configured to
receive the signaling containing information about the acoustic signal injected into the mixture of concrete; and
determine the measurement of air percentage in the mixture of concrete based at least partly on a dual frequency technique that depends on the relationship between the acoustic signal injected and the signaling received.

39. Apparatus according to claim 38, wherein the dual frequency technique includes, or takes the form of, the signal processor being configured to determine the measurement of air percentage in the mixture of concrete based at least partly on mixing a reference signal with a detected signaling using a phase sensitive lock-in approach.

40. Apparatus according to claim 38, wherein the dual frequency technique includes, or takes the form of, the signal processor being configured to determine the measurement of air percentage in the mixture of concrete based at least partly on correlating the acoustic signal injected and the signaling received.

41. Apparatus according to claim 34, wherein the acoustic source comprises a piston module assembly having a rigid hardened steel piston configured to be coupled to a piston shaft.

42. Apparatus according to claim 41, wherein the acoustic-based air probe comprises a vibration isolated actuator block assembly having a stationary voice coil actuator field assembly in combination with a voice coil actuator field assembly having an accelerometer transducer, the vibration isolated actuator block assembly being configured to drive the piston shaft.

43. Apparatus according to claim 34, wherein the acoustic receiver comprises a dynamic pressure transducer.

44. Apparatus according to claim 34, wherein the acoustic receiver is configured to receive acoustic signals having a frequency in a range of about 100-500 Hz, including 330 Hz.

45. Apparatus according to claim 34, wherein the apparatus comprises a signal processor configured to
receive the signaling containing information about the acoustic signal injected into the mixture of concrete; and
determine a gas volume fraction of the mixture of concrete based at least partly on a speed of sound measurement of the acoustic signal that travels through the mixture, using a SONAR-based technique.

46. Apparatus comprising:
an acoustic-based air probe having;
an acoustic source configured to provide acoustic signal into a mixture of concrete; and
an acoustic receiver configured to be substantially co-planar with the acoustic source, to respond to the acoustic signal, and to provide signaling containing information about the acoustic signal injected into the mixture of concrete;
wherein the acoustic-based air probe comprises a fluid/media temperature sensor for providing the temperature of the mixture of concrete.

47. Apparatus according to claim 46, wherein the acoustic-based air probe comprises a planar probing surface having a first aperture formed therein configured to receive part of the acoustic source.

48. Apparatus according to claim 47, wherein the planar probing surface has at least one second aperture formed therein configured to receive part of the acoustic receiver.

49. Apparatus according to claim 47 or 48, wherein the planar probing surface is configured as a hardened steel face plate.

50. Apparatus according to claim 46, wherein the acoustic source comprises a piston module assembly having a rigid hardened steel piston configured to be coupled to a piston shaft.

51. Apparatus according to claim 50, wherein the acoustic-based air probe comprises a vibration isolated actuator block assembly having a stationary voice coil actuator field assembly in combination with a voice coil actuator field assembly having an accelerometer transducer, the vibration isolated actuator block assembly being configured to drive the piston shaft.

52. Apparatus according to claim 46, wherein the acoustic-based air probe comprises a protective polyurethane rubber member arranged in the at least one second aperture.

53. Apparatus according to claim 46, wherein the acoustic receiver comprises a dynamic pressure transducer.

54. Apparatus according to claim 46, wherein the acoustic receiver is configured to receive acoustic signals having a frequency in a range of about 100-500 Hz, including 330 Hz.

55. Apparatus according to claim 46, wherein the acoustic source comprises a floating mass.

56. Apparatus comprising:
an acoustic-based air probe having;
an acoustic source configured to provide and acoustic signal into a mixture of concrete; and
an acoustic receiver configured to be substantially co-planar with the acoustic source, to respond to the acoustic signal, and to provide signaling containing information about the acoustic signal injected into the mixture of concrete;
wherein the acoustic-based air probe comprises a planar probing surface having a first aperture formed therein configured to receive part of the acoustic source;
wherein the planar probing surface has at least one second aperture formed therein configured to receive part of the acoustic receiver; and
wherein the acoustic-based air probe comprises a protective polyurethane rubber member arranged in the at least one second aperture.

57. Apparatus according to claim 56, wherein the acoustic source comprises a piston module assembly having a rigid hardened steel piston configured to be coupled to a piston shaft.

58. Apparatus according to claim 57, wherein the acoustic-based air probe comprises a vibration isolated actuator block assembly having a stationary voice coil actuator field assembly in combination with a voice coil actuator field assembly having an accelerometer transducer, the vibration isolated actuator block assembly being configured to drive the piston shaft.

59. Apparatus according to claim 56, wherein the planar probing surface is configured as a hardened steel face plate.

60. Apparatus according to claim 56, wherein the acoustic receiver comprises a dynamic pressure transducer.

61. Apparatus according to claim 56, wherein the acoustic receiver is configured to receive acoustic signals having a frequency in a range of about 100-500 Hz, including 330 Hz.

62. Apparatus according to claim 56, wherein the acoustic source comprises a floating mass.

63. Apparatus comprising:
an acoustic-based air probe having;
an acoustic source configured to provide an acoustic signal into a mixture of concrete; and
an acoustic receiver configured to be substantially co-planar with the acoustic source, to respond to the acoustic signal, and to provide signaling containing information about the acoustic signal injected into the mixture of concrete;
wherein the acoustic-based air probe comprises a voice coil temperature sensor for providing the temperature of a stationary voice coil actuator field assembly.

64. Apparatus according to claim 63, wherein the acoustic-based air probe comprises a planar probing surface having a first aperture formed therein configured to receive part of the acoustic source.

65. Apparatus according to claim 63, wherein the acoustic-based air probe comprises a protective polyurethane rubber member arranged in the at least one second aperture.

66. Apparatus according to claim 63, wherein the acoustic receiver comprises a dynamic pressure transducer.

67. Apparatus according to claim 63, wherein the acoustic source comprises a floating mass.

68. Apparatus comprising:
an acoustic-based air probe having;
an acoustic source configured to provide an acoustic signal into a mixture of concrete; and
an acoustic receiver configured to be substantially co-planar with the acoustic source, to respond to the acoustic signal, and to provide signaling containing information about the acoustic signal injected into the mixture of concrete;
wherein the acoustic-based air probe comprises two acoustic receivers, including two dynamic pressure transducers, including where one of the two acoustic receivers is redundant.

* * * * *